(12) United States Patent
Haber

(10) Patent No.: US 8,794,964 B2
(45) Date of Patent: *Aug. 5, 2014

(54) COMPUTER-AIDED DESIGN OF A DRILL GUIDE WITH A WINDOW

(75) Inventor: Jerome Haber, Weston, MA (US)

(73) Assignee: Guided Surgery Solutions, LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,737

(22) Filed: Jun. 18, 2010

(65) Prior Publication Data

US 2011/0111364 A1 May 12, 2011

Related U.S. Application Data

(63) Continuation of application No. 12/816,710, filed on Jun. 16, 2010.

(60) Provisional application No. 61/260,065, filed on Nov. 11, 2009.

(51) Int. Cl.
*A61C 3/00* (2006.01)
*A61C 1/08* (2006.01)

(52) U.S. Cl.
CPC .................................... *A61C 1/084* (2013.01)
USPC .............................................. 433/75; 606/96

(58) Field of Classification Search
USPC ............ 433/72, 75–76, 173, 196; 606/96–97
See application file for complete search history.

(56) References Cited

U.S. PATENT DOCUMENTS

| 3,838,517 | A | | 10/1974 | Michnick |
| 4,998,881 | A | | 3/1991 | Lauks |
| 5,015,183 | A | | 5/1991 | Fenick |
| 5,133,660 | A | * | 7/1992 | Fenick ............................ 433/76 |

(Continued)

FOREIGN PATENT DOCUMENTS

| EP | 1502556 | 2/2005 |
| WO | WO-2009119620 | 10/2009 |
| WO | WO 2011/059899 A1 | 5/2011 |

OTHER PUBLICATIONS

"U.S. Appl. No. 12/816,710, Non-Final Office Action mailed Sep. 20, 2011", 13.

(Continued)

*Primary Examiner* — Cris L Rodriquez
*Assistant Examiner* — Hao D Mai
(74) *Attorney, Agent, or Firm* — Strategic Patents, P.C.

(57) ABSTRACT

A drill guide uses a hole in a layer to guide a drill along an axial trajectory while permitting off-axis excursions of the drill during use. A number of such drill guides at varying heights from a target surface may be used sequentially or concurrently to enforce the axial trajectory in three dimensions during a surgical operation. A drill guide may include a hole in a layer that establishes a single point along the axial trajectory, or the drill guide may include multiple layers in a single device to establish two or more points along the trajectory while allowing off-axis insertion of a drill into the guide. The drill guide may be cuttable to accommodate intraoperative changes to the axial trajectory. In embodiments, a window or the like may be provided to permit a surgeon to view drill depth, drill orientation, the surgical site and the like during a procedure.

17 Claims, 12 Drawing Sheets

(56) References Cited

U.S. PATENT DOCUMENTS

| | | | |
|---|---|---|---|
| 5,320,529 | A | 6/1994 | Pompa |
| 5,439,381 | A | 8/1995 | Cohen |
| 5,641,287 | A | 6/1997 | Gittleman |
| 5,718,579 | A | 2/1998 | Kennedy |
| 5,768,134 | A | 6/1998 | Swaelens et al. |
| 5,833,693 | A | 11/1998 | Abrahami |
| 5,927,919 | A | 7/1999 | Blankenship |
| 5,967,777 | A | 10/1999 | Klein |
| 6,390,814 | B1 | 5/2002 | Gardiner |
| 6,739,872 | B1 | 5/2004 | Turri |
| 6,966,772 | B2 * | 11/2005 | Malin et al. ............. 433/75 |
| 6,971,877 | B2 * | 12/2005 | Harter ............. 433/75 |
| 7,044,735 | B2 | 5/2006 | Malin |
| 7,097,451 | B2 | 8/2006 | Tang |
| 7,104,795 | B2 | 9/2006 | Dadi |
| 7,331,786 | B2 | 2/2008 | Poirier |
| 7,364,388 | B2 | 4/2008 | Faul et al. |
| 7,615,047 | B2 | 11/2009 | Berna et al. |
| 7,845,943 | B2 * | 12/2010 | Meitner ............. 433/75 |
| 7,905,726 | B2 | 3/2011 | Stumpel |
| 8,135,492 | B2 | 3/2012 | Yau et al. |
| 8,333,587 | B2 * | 12/2012 | Jamison ............. 433/75 |
| 2004/0219478 | A1 * | 11/2004 | Harter ............. 433/75 |
| 2004/0219479 | A1 | 11/2004 | Malin et al. |
| 2004/0219480 | A1 * | 11/2004 | Malin ............. 433/75 |
| 2004/0219481 | A1 | 11/2004 | Malin et al. |
| 2004/0249370 | A1 | 12/2004 | Berna et al. |
| 2005/0170311 | A1 | 8/2005 | Tardieu et al. |
| 2005/0182317 | A1 | 8/2005 | Haddad |
| 2006/0093988 | A1 | 5/2006 | Swaelens et al. |
| 2006/0257817 | A1 | 11/2006 | Shelton |
| 2006/0263743 | A1 | 11/2006 | Tedesco |
| 2007/0154862 | A1 | 7/2007 | Kim |
| 2007/0154866 | A1 | 7/2007 | Hall |
| 2007/0298374 | A1 | 12/2007 | Carlton |
| 2008/0026338 | A1 | 1/2008 | Cinader |
| 2008/0085489 | A1 | 4/2008 | Schmitt |
| 2008/0166681 | A1 | 7/2008 | Weinstein et al. |
| 2008/0176187 | A1 | 7/2008 | Stumpel |
| 2008/0227056 | A1 | 9/2008 | Bulard |
| 2009/0004625 | A1 | 1/2009 | Esposti et al. |
| 2009/0011382 | A1 | 1/2009 | Bavar |
| 2009/0136902 | A1 | 5/2009 | Zundorf |
| 2009/0202959 | A1 | 8/2009 | Ajlouni et al. |
| 2009/0263764 | A1 | 10/2009 | Berckmans, III et al. |
| 2010/0173259 | A1 * | 7/2010 | Vogel et al. ............. 433/72 |
| 2010/0203479 | A1 | 8/2010 | Bulloch et al. |
| 2010/0255441 | A1 | 10/2010 | Taormina |
| 2010/0256649 | A1 * | 10/2010 | Capsal et al. ............. 606/96 |
| 2011/0111362 | A1 | 5/2011 | Haber |
| 2011/0111363 | A1 | 5/2011 | Haber |
| 2011/0111371 | A1 | 5/2011 | Haber |
| 2011/0112544 | A1 | 5/2011 | Haber |
| 2011/0143307 | A1 | 6/2011 | Takebayashi |
| 2011/0151399 | A1 * | 6/2011 | De Clerck et al. ............. 433/75 |
| 2013/0144422 | A1 | 6/2013 | Choi et al. |

OTHER PUBLICATIONS

"International Application Serial No. PCT/US2010/055779, Search Report and Written Opinion mailed Mar. 23, 2011", 13.

"U.S. Appl. No. 12/818,601, Non-Final Office Action mailed Jul. 22, 2011", 12.

Choi, M et al., "Surgical Guide for Implant Placement: Effects on Implant Angulation", *32nd Annual Meeting and Exhibition of the AADR* (Mar. 12-15, 2003) Research report.

Sarment, David P. et al., "Diagnostic Casts and Surgical Templates", all.

"U.S. Appl. No. 12/818,601, Notice of Allowance mailed May 3, 2012", U.S. Appl. No. 12/818,601—NoA NPL-14 May 3, 2012, 8 pages.

Haber, Jerome, DDS, DMSC. , "Computer Guided Implant Treatment Minimally Invasive Surgery", Dentsply Tulsa Dental Specialties NPL-9 Dec. 5, 2007, pp. 1-168.

"Reverse Guide Implant Technique", Trinon Collegium Practicum Trinon Titanium GmbH Karlsruhe Germany NPL-8 Nov. 3, 2009, pp. 1-2.

"U.S. Appl. No. 12/818,522, Non-Final Office Action mailed Dec. 21, 2011", 17.

"U.S. Appl. No. 12/816,710, Final Office Action mailed Dec. 8, 2011", 11.

"U.S. Appl. No. 12/818,601, Final Office Action mailed Dec. 14, 2011", 14.

"U.S. Appl. No. 12/818,824 Non-Final Office Action mailed Jul. 12, 2012", U.S. Appl. No. 12/818,824—NFOA NPL-16 Jul. 12, 2012, 20 pgs.

"U.S. Appl. No. 12/818,824 Non-Final Office Action mailed Jun. 5, 2013", 16 pages.

"U.S. Appl. No. 12/816,710, Non-Final Office Action mailed Mar. 1, 2013", 13 pages.

"U.S. Appl. No. 12/818,522, Final Office Action mailed Mar. 12, 2013", 17 pages.

"U.S. Appl. No. 12/816,710, Final Office Action mailed Oct. 16, 2013", 11 pages.

"U.S. Appl. No. 12/818,522, Non-Final Office Action mailed Jun. 21, 2013", 9 pages.

"U.S. Appl. No. 12/816,710, Notice of Allowance mailed Mar. 31, 2014", pp. 1-15.

"U.S. Appl. No. 12/818,522, Non-Final Office Action mailed Mar. 21, 2014", 11 pages.

"U.S. Appl. No. 12/818,601, Notice of Allowance mailed Feb. 26, 2014", 22 pages.

"EP Application Serial No. 10830553.3, European Search Report mailed Apr. 9, 2014", 7 Pages.

* cited by examiner

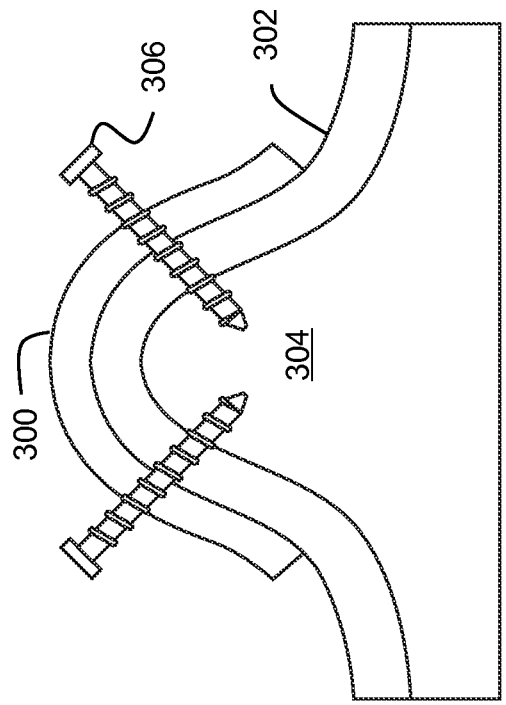
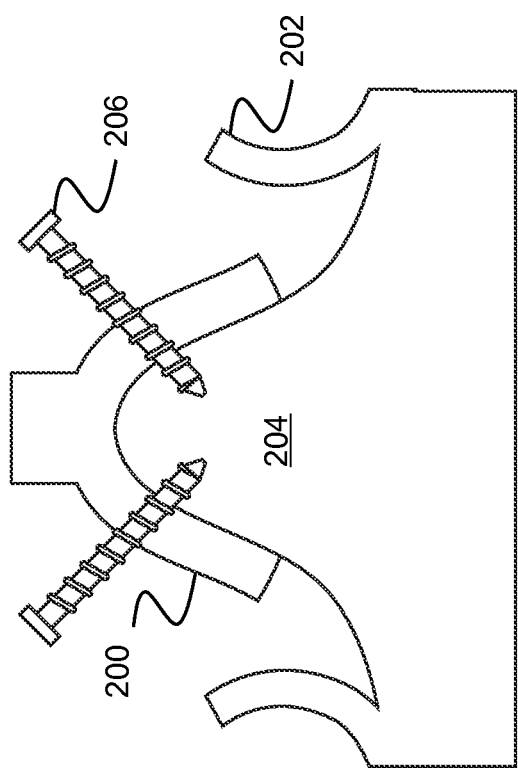
Fig. 3
Fig. 2

COMPUTER-AIDED DESIGN OF A DRILL GUIDE WITH A WINDOW

RELATED APPLICATIONS

This application is a continuation of U.S. application Ser. No. 12/816,710 filed Jun. 16, 2010 which claims the benefit of U.S. Prov. App. No. 61/260,065 filed on Nov. 11, 2009, each of which is hereby incorporated by reference.

BACKGROUND

The invention relates to surgical drill guides for use in dental surgery and similarly constrained surgical and/or drilling operations.

Drill guides are commonly used by dental surgeons to align a drill or other cutting tool with an intended hole for a dental implant; however, existing drill guides have significant disadvantages. For example, some drill guides require insertion of a drill in alignment with a cutting trajectory, which can present difficulties in confined spaces that offer little clearance or overhead. As another disadvantage, some drill guides block a surgeon's view of the location where a drill meets bone or other tissue, thus impairing the surgeon's ability to obtain adequate visual verification of drill position and depth.

There remains a need for improved drill guide devices and methods for use in dental surgery and similarly constrained surgical and/or drilling operations.

SUMMARY

A drill guide uses a hole in a layer to guide a drill along an axial trajectory while permitting off-axis excursions of the drill during use. A number of such drill guides at varying heights from a target surface may be used sequentially or concurrently to enforce the axial trajectory in three dimensions during a surgical operation. A drill guide may include a hole in a layer that establishes a single point along the axial trajectory, or the drill guide may include multiple layers in a single device to establish two or more points along the trajectory while allowing off-axis insertion of a drill into the guide. The drill guide may be cuttable to accommodate intraoperative changes to the axial trajectory. In embodiments, a window or the like may be provided to permit a surgeon to view drill depth, drill orientation, the surgical site and the like during a procedure.

In one aspect, a device disclosed herein includes: a surgical guide for a dental procedure, the surgical guide including a first hole in a first layer, the first hole positioned to align a tool to an axial trajectory at a first point along the axial trajectory and the surgical guide including a second hole in a second layer, the second layer vertically spaced apart from the first layer along the axial trajectory and the second hole positioned to align the tool to the axial trajectory at a second point along the axial trajectory; and a support to secure the surgical guide in relation to a location where the axial trajectory meets a target surface of a surgical site.

The target surface may include one or more of soft tissue and bone. The target surface may include one or more of gingiva and a jawbone. The surgical site may include a dental implant site. The axial trajectory may be a trajectory of a surgical drill into a surgical site. The axial trajectory may be a trajectory of a surgical drill into a dental implant site. The first hole and the second hole may be shaped and sized to align an object to the axial trajectory including one or more of a drill, a surgical drill, a rotary tool, and a surgical hand tool. The support may include a surface formed to dentition around the surgical site, thereby providing tooth support for the surgical guide. The surface may be formed to a full arch containing the surgical site. The support may include a surface formed to bone around the surgical site, thereby providing bone support for the surgical guide. The support may include one or more bone attachment points for securing the device to a jawbone. The support may include a surface formed to soft tissue around the surgical site, thereby providing soft tissue support for the surgical guide. The support may be shaped and sized to provide gingival support for the surgical guide. The support may be shaped and sized to provide skin support for the surgical guide. The first layer may contact the target surface in an area surrounding the first hole when the device is placed for use at the surgical site. The second layer may be spaced apart from the target surface in an area surrounding the second hole when the device is placed for use at the surgical site.

The second hole may have a diameter larger than the first hole. The device may further include a space between the first layer and the second layer that permits an insertion of the tool off-axis from the axial trajectory. The second layer may include one or more visible alignment marks to assist a user in locating a center of the first hole. The first layer may include one or more additional visible alignment marks to assist the user in locating a center of the second hole. The device may include an opening for physical access to a space between the first layer and the second layer. The device may include an opening for physical access to the surgical site. The device may include a window for visual inspection of the target surface while the surgical guide may be in use. The device may include a window for visual inspection of the axial trajectory between the first layer and the second layer. The device may be fabricated from a cuttable material. The axial trajectory may be modified by enlarging one or more of the first hole and the second hole. The device may include a plurality of holes in each of the first layer and the second layer for a plurality of axial trajectories.

The device may include a plurality of devices each including a third hole positioned to align one of a number of progressively larger diameter drills to the first point on the axial trajectory. Each of the plurality of devices further may include a fourth hole positioned to align one of the number of progressively larger diameter drills to the second point on the axial trajectory. At least one of the first hole and the second hole may have a sleeve that protects the surgical guide against a cutting edge of the tool. The sleeve may be formed of a material including one or more of a steel, a titanium, a glass, a plastic, and an aluminum. The surgical guide and the support may be formed of a clear material. The second hole may have a larger diameter than the first hole, the second hole sized to accommodate a drill stop and the first hole sized to accommodate a drill without the drill stop.

In another aspect, a method disclosed herein include obtaining three-dimensional data from beneath a surface of a surgical site; determining an axial trajectory for an implant to be placed in the surgical site based upon the three-dimensional data; and fabricating a device based upon the three-dimensional data, the device including a support fitted to an area around the surgical site and a surgical guide including a hole that aligns a tool to the axial trajectory at a first point along the axial trajectory while permitting off-axis excursions of the tool from the axial trajectory at a second point along the axial trajectory away from the hole when the surgical guide may be placed for use at the surgical site.

Fabricating the device may include manually fabricating the support and applying the three-dimensional data to create the hole in the surgical guide. Fabricating the device may include applying the three-dimensional data to generate a digital model of the surgical guide including the hole and fabricating the surgical guide from the digital model. Determining the axial trajectory for the implant may include positioning an implant with implant planning software. Fabricating the device may include applying the three-dimensional data to create the hole in the digital model of the device. Fabricating the device may include: capturing a physical impression of the surgical site; using the physical impression to fabricate a physical model; and using the physical model to manually fabricate the device. Obtaining three-dimensional data may include obtaining x-ray tomography data of the device and applying the three-dimensional data to create a digital model of the device. Fabricating the device may include applying the three-dimensional model to a computerized fabrication system to fabricate the surgical guide. The method may include creating the hole in the surgical guide with a computer-controlled machine. The computer-controlled machine may include a computer-controlled milling machine. The computer-controlled machine may include a computer-controlled drilling machine. The computer-controlled machine may include one or more of a hole punch and a heated probe.

Obtaining three-dimensional data may include obtaining x-ray tomography data from the surgical site. Obtaining three-dimensional data may include creating a digital three-dimensional surface model of the surgical site. Obtaining three-dimensional data may include creating a digital three-dimensional surface model of at least a portion of a dental arch. Obtaining three-dimensional data may include creating a digital three-dimensional surface model of a full dental arch. Fabricating the device may include using the digital three-dimensional surface model to fabricate the device using a computerized fabrication system. The computerized fabrication system may include a stereolithography system. The computerized fabrication system may include a computerized milling machine. Fabricating the device may include forming a material to a physical model of a dental arch containing the surgical site. Forming the material to the physical model may include forming a sheet of material onto the physical model. Forming the material to the physical model may include vacuum forming a plastic sheet onto the physical model. The surgical site may include one or more of soft tissue and bone. The surgical site may include one or more of gingiva and a jawbone. The axial trajectory may be a trajectory of a surgical drill into the surgical site. The axial trajectory may be a trajectory of a surgical drill into a dental implant site. The method may include adding one or more visible alignment marks to assist a user in locating a center of the hole. Fabricating the device may include fabricating the surgical guide from a clear material. Fabricating the device may include fabricating the support to secure the surgical guide in a desired location relative to the surgical site. The support may include a surface formed to dentition around the surgical site, thereby providing tooth support for the surgical guide. The surface may be formed to a full arch containing the surgical site. The support may provide bone support for the surgical guide.

The method may include adding one or more bone attachment points to the support for securing the support to a jawbone, thereby providing bone support for the surgical guide. The support may provide soft tissue support for the surgical guide. The support may provide gingival support for the surgical guide. The support may provide skin support for the surgical guide.

Fabricating the device may include fabricating a two-layer surgical guide having a first hole in a first layer centered around a first point on the axial trajectory and a second hole in a second layer centered about a second point on the axial trajectory. Obtaining three-dimensional data may include obtaining a digital three-dimensional surface model of the surgical site. Fabricating the device may include using the digital three-dimensional surface model to fabricate the surgical guide using a computerized fabrication system. The computerized fabrication system may include a stereolithography system. The computerized fabrication system may include a computerized milling machine. The axial trajectory may intersect a target surface of the surgical site when the surgical guide may be placed for use at the surgical site and the second layer may be vertically spaced apart from the target surface in a second area surrounding the second hole. The first layer and the second layer may be vertically spaced apart to provide a space that permits an insertion of the tool off-axis from the axial trajectory. Fabricating the device may include fabricating a window for physical access to a space between the first layer and the second layer. Fabricating the device may include fabricating a window for visual inspection of a target surface while the surgical guide may be in use. Fabricating the device may include fabricating a window for visual inspection of the axial trajectory between the first layer and the second layer.

Fabricating the device may include fabricating the device from a cuttable material wherein the axial trajectory can be modified by enlarging the hole. Fabricating the device may include fabricating the device with a plurality of holes for a plurality of axial trajectories. Fabricating a plurality of devices each including a progressively larger diameter hole shaped and positioned to align one of a number of progressively larger diameter drills to the first point on the axial trajectory. The method may include adding a sleeve to the hole that protects the surgical guide against a cutting edge of the tool. The sleeve may be formed of a material including one or more of a steel, a titanium, a glass, a plastic, and an aluminum. Fabricating the device may include fabricating a window for visual inspection of the surgical site. Fabricating the surgical guide may include fabricating a window for physical access to the surgical site.

In another aspect, a method for realizing an axial trajectory of a cutting process disclosed herein includes: guiding a first cutting tool with a first guide at a first point along the axial trajectory when the first guide may be positioned for use at a surgical site while permitting movement of the first cutting tool away from the axial trajectory at one or more other points along the axial trajectory; and guiding a second cutting tool with a second guide at a second point along the axial trajectory vertically spaced apart from a target surface when the second guide may be positioned for use at the surgical site while permitting movement of the second cutting tool away from the axial trajectory at the one or more other points along the axial trajectory.

The first point may lie on the axial trajectory where the axial trajectory intersects a target surface. The first cutting tool may be the same as the second cutting tool. The second cutting tool may have a larger diameter than the first cutting tool. The method may include guiding a plurality of progressively larger diameter drills with the second guide. The method may include providing a plurality of guides with a respective plurality of larger holes for at least one of the first point and the second point along the axial trajectory. The target surface may be a dental implant site. The target surface may be a surgical site. At least one of the first cutting tool and the second cutting tool may include one or more of a drill, a surgical drill, a rotary tool, and a surgical hand tool. The first guide and the second guide may be integrated into a single device for concurrent use. The method may include supporting the single device with a support including one or more of a bone support, a tooth support, and a soft tissue support. The first guide and the second guide may be physically separate devices. The first guide and the second guide may include progressively larger holes and the first guide and the second guide may be progressively applied to enforce the axial trajectory for progressively larger tools. The method may include supporting one of the physically separate devices with a support including one or more of a bone support, a tooth support, and a soft tissue support.

At least one of the first cutting tool and the second cutting tool may include a drill with a drill stop. At least one of the first guide and the second guide may include a window for visual access to the surgical site when placed for use at the surgical site. At least one of the first guide and the second guide may include a window for physical access to the surgical site when placed for use at the surgical site. The first guide may include one or more visible alignment marks to assist a user in centering the first cutting tool on the axial trajectory. The second guide may include one or more visible alignment marks to assist a user in centering the second cutting tool on the axial trajectory. At least one of the first guide and the second guide may be formed of a cuttable material. The method may include cutting at least one of the first guide and the second guide to adjust the axial trajectory. The first guide may include a hole for the first cutting tool, and the method may include adding a sleeve to the hole to protect against a cutting edge of the first cutting tool. The second guide may include a hole for the second cutting tool, and the method may include adding a sleeve to the hole to protect against a cutting edge of the second cutting tool. At least one of the first guide and the second guide may be formed of a clear material.

In another aspect, a method disclosed herein includes obtaining three-dimensional data from beneath a target surface of a surgical site; determining an axial trajectory for an implant to be placed in the surgical site based upon the three-dimensional data; and fabricating a device, the device including: a surgical guide formed of a hole in a layer that aligns a tool to the axial trajectory when the surgical guide may be placed for use at the surgical site; an interior space along the axial trajectory within the device; a window in a side of the device for access to the interior space; and a support to secure the surgical guide in relation to the surgical site.

The three-dimensional data from beneath the target surface may include non-surface, interior data from within one or more dental structures. Access to the interior space may include physical access. Access to the interior space may include visual access. The layer may be a thin layer that permits movement of the tool away from the axial trajectory at one or more points along the axial trajectory. The interior space may be between the layer and the target surface when the device may be placed for use at the surgical site. The layer may be a thick layer that confines the tool to the axial trajectory. The window may provide a view of the axial trajectory where the axial trajectory intersects the target surface when the device may be placed for use at the surgical site. The window may provide a view of the axial trajectory where the axial trajectory intersects the layer. The window may include a transparent surface of the device. The axial trajectory may be a trajectory of a surgical drill into a dental implant site. The axial trajectory may be a trajectory of a surgical drill into the surgical site. The target surface may include one or more of soft tissue and bone. The target surface may include one or more of gingiva and a jawbone. The surgical site may include a dental implant site.

The hole may be shaped and sized to align an object including one or more of a drill, a surgical drill, a rotary tool, and a surgical hand tool to the axial trajectory. The support may include a surface formed to dentition around the surgical site, thereby providing tooth support for the surgical guide. The surface may be formed to a full arch containing the surgical site. The support may be shaped and sized to provide bone support for the surgical guide. The support may include one or more bone attachment points for securing the surgical guide to a jawbone, thereby providing bone support for the surgical guide. The support may be shaped and sized to provide soft tissue support for the surgical guide. The support may be shaped and sized to provide gingival support for the surgical guide. The support may be shaped and sized to provide skin support for the surgical guide.

The layer may contact the target surface in an area surrounding the hole when the surgical guide is placed for use at the surgical site. The layer may be spaced apart from the target surface in an area surrounding the hole when the surgical guide is placed for use at the surgical site. The window may be positioned between the layer and the target surface. The window may be positioned between the layer and a second layer that abuts the target surface. The interior space may be coextensive with the hole. The interior space may include a volume between the layer and the target surface that permits an insertion of the tool off-axis from the axial trajectory. The surgical guide may include a second hole in a second layer that aligns the tool to the axial trajectory when the surgical guide may be placed for use at the surgical site. Fabricating the surgical guide may include fabricating the surgical guide from a cuttable material. The method may include modifying the axial trajectory by enlarging the hole.

The surgical guide may include a plurality of holes in the layer for a plurality of axial trajectories at different locations in a dental arch. The method may include fabricating a plurality of surgical guides, each including a progressively larger hole to align one of a number of progressively larger diameter drills to the axial trajectory. The method may include adding a sleeve to the hole that protects the surgical guide against a cutting edge of the tool. The sleeve may be formed of a material including one or more of a steel, a titanium, a glass, a plastic, and an aluminum.

In another aspect, a device disclosed herein includes a surgical guide, the surgical guide including a hole in a layer, the hole positioned to align a tool to an axial trajectory at a first point along the axial trajectory, and the hole including a tapered wall that provides a diameter that varies along an axis of the hole, wherein the diameter ranges between a narrowest section and a widest section; and a support to secure the surgical guide in relation to a location where the axial trajectory meets a target surface of a surgical site.

The device may include a second hole in a second layer vertically spaced apart from the first layer, the second hole positioned to align the tool to the axial trajectory at a second point along the axial trajectory. The target surface may include one or more of soft tissue and bone. The target surface may include one or more of gingiva and a jawbone. The surgical site may include a dental implant site. The axial trajectory may be a trajectory of a surgical drill into a surgical site. The axial trajectory may be a trajectory of a surgical drill into a dental implant site. The hole may be shaped and sized to align an object to the axial trajectory including one or more of a drill, a surgical drill, a rotary tool, and a surgical hand tool. The support may include a surface formed to dentition around the surgical site, thereby providing tooth support for the surgical guide. The support may include a surface formed to bone around the surgical site, thereby providing bone support for the surgical guide. The support may include one or more bone attachment points for securing the device to a jawbone. The support may include a surface formed to soft tissue around the surgical site, thereby providing soft tissue support for the surgical guide. The layer may be vertically spaced apart from the target surface in an area surrounding the hole when the device may be placed for use at the surgical site. The layer may include one or more visible alignment marks to assist a user in locating a center of the hole.

The device may include a window for visual inspection of the target surface while the surgical guide may be in use. The device may include a window for physical access to the surgical site when the device may be placed for use. The device may be fabricated from a cuttable material. The device may include a plurality of holes in the layer for a plurality of axial trajectories. The hole may include a sleeve that protects the surgical guide against a cutting edge of the tool. The sleeve may be formed of a material including one or more of a steel, a titanium, a glass, a plastic, and an aluminum. The surgical guide and the support may be formed of a clear material. The layer may have a thickness less than the diameter of the hole at the widest section. The layer may have a thickness less than the diameter of the hole at the narrowest section. The layer may have a thickness greater than the diameter of the hole at the narrowest section. The layer may have a thickness greater than the diameter of the hole at the widest section. The diameter of the hole at the widest section may be at least ten percent greater than the diameter of the hole at the narrowest section. The diameter of the hole at the widest section may be at least twenty-five percent greater than the diameter of the hole at the narrowest section. The widest section may be on a top of the layer and the narrowest section may be on a bottom of the layer. The narrowest section may be at a surface of the layer proximal to the location where the axial trajectory meets the target surface of the surgical site. The narrowest section may be at a surface of the layer distal to the location where the axial trajectory meets the target surface of the surgical site. The narrowest section may be between a top surface and a bottom surface of the layer.

BRIEF DESCRIPTION OF THE DRAWINGS

The foregoing and other objects, features and advantages of the invention will be apparent from the following description of particular embodiments thereof, as illustrated in the accompanying drawings in which like reference characters refer to the same parts throughout the different views. The drawings are not necessarily to scale, emphasis instead being placed upon illustrating the principles of the invention.

FIG. 2 illustrates bone support for a surgical guide.

FIG. 3 illustrates soft tissue and bone support for a surgical guide.

DETAILED DESCRIPTION

Described herein are devices and methods for enforcing an axial trajectory during a drilling operation. In particular, exemplary embodiments of the invention include devices and methods for guiding a surgical drill along a predetermined axial trajectory during a dental implant procedure. As used herein, the term "axial trajectory" refers to a straight line defined by at least two separate points that characterize an intended path (typically the center of the path) for a drill into a site such as a surgical site. The axial trajectory for a particular surgical operation may be determined, for example, using planning software or the like prior to the surgical operation based upon three-dimensional data acquired from the surgical site. It will be understood that while the following description depicts lower-jaw drill guides, one of ordinary skill in the relevant art may readily adapt the surgical guides and related procedures to an upper jaw, and all such variations are intended to fall within the scope of this disclosure.

Figure 1:
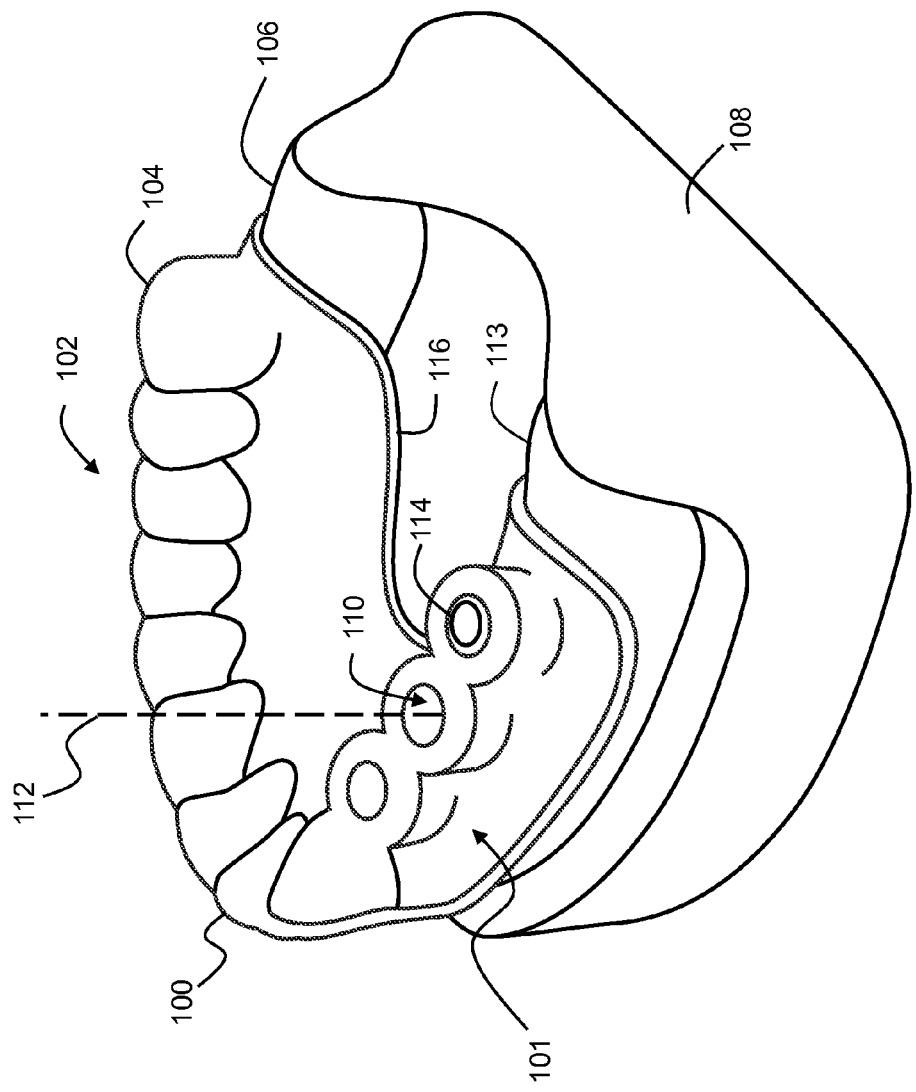
FIG. 1 shows a surgical drill guide for dental applications.

FIG. 1 shows a device 100 including a surgical guide 101 and a support 102. In general, the surgical guide 101, which may be a surgical drill guide for use in dental procedures or the like, may include one or more holes 110 to align a drill with an axial trajectory 112. The support 102 may be fitted to the teeth 104, soft tissue 106, and/or bone 108 in order to retain the surgical guide 101 relatively immobile with respect to the bone 108 during a drilling operation. It will be understood that while terms such as "surgical guide" or "drill guide" are typically used in the art to describe the entire device 100 depicted in FIG. 1, the following description refers periodically to a "surgical guide" instead as that portion of such a device 100 that physically retains a drill or other tool or object along the axial trajectory 112 in order to distinguish this functional portion from the support 102, which operates to secure the surgical guide 101 (and the axial trajectory 112 defined by same) relative to a target location. Thus depending on the context a "surgical guide" as used herein may refer specifically to a portion of a device that has one or more holes (or other guiding elements), or may refer generally to an entire device that is used as a drill guide or the like.

The support 102 may be fabricated to conform to any features within a patient's mouth including the teeth 104, soft tissue 106, and bone 108. This design may be derived for example from a model of a patient's dental arch or from three-dimensional digital scans or other three-dimensional data from a surgical site. In general, the support 102 secures the surgical guide 101 in relation to a location where the axial trajectory 112 meets a target surface 113.

The support 102 may provide tooth support, soft tissue support, and/or bone support. As depicted, the support 102 may include a surface 116 (the interior surface of the device 100) formed to dentition around a dental implant site, thus providing tooth support. The surface 116 may be formed to a full arch containing the dental implant site, or some portion thereof. The support 102 may also or instead provide soft tissue support with the surface 116. This may include skin support, gingival support, or more generally any soft tissue support by which the surface 116 is formed to the skin, gingiva, gum, mucosa, and the like. The support 102 may also, or instead, provide bone support, which may in use involve supplemental surgical procedures such as cutting and lifting a flap of the soft tissue 106 to expose the bone 108 so that the surface 116 can be placed in direct contact with the bone 108, or using one or more screws or other attachments to secure the support 102 directly to the bone 108. More generally, the support 102 may provide support to fix the surgical guide 101 relative to the bone 108 using any or all of the above techniques, and the support 102 may usefully cover more or less of the dentition and surrounding tissue than depicted, all without departing from the scope of this disclosure.

While not visible in FIG. 1, it will be appreciated that the target surface 113 extends to a location beneath the surgical guide 101 where the axial trajectory 112 intersects the soft tissue 106 or bone 108 so that a drill or other tool may be directed into the jaw at an appropriate location and orientation. As used herein, the term "target surface" is generally intended to refer to an exterior, two-dimensional surface of a surgical site that includes a location where a drill, tool, or implant is intended to enter the surgical site, unless a different meaning is specifically provided or otherwise clear from the context. In general, the target surface follows surface contours of a dental arch that is prepared for surgery and includes a single point of intersection with the axial trajectory 112. The target surface 113 may include any soft tissue 106 or bone 108 as described herein.

While the systems and methods described below are useful in dental surgery, it will be appreciated that these systems and methods may more generally be used at a surgical site, which as used herein is intended to refer to a volume surrounding and including a location where surgery will be performed. This may include a dental implant site where a dental implant is to be placed in a jawbone or more generally any site along the dental arch or elsewhere that a drill or other cutting tool might usefully be guided in a surgical procedure.

FIG. 2 illustrates bone support for a surgical guide. In a bone supported guide 200, a flap of the soft tissue 202 may be cut and lifted as illustrated in order to expose the bone 204 underlying the soft tissue 202. In other embodiments, a portion of the gum may be cut away using a punch or similar device to expose the underlying bone around the drill site. One or more screws 206 may also be used to secure the bone supported guide 200 to the bone 204. It will be appreciated that, while introduced in the context of a prior art drill guide, bone support may also be used with the drill guides described below.

FIG. 3 illustrates soft tissue and bone support for a surgical guide. The guide 300 may be placed directly in contact with soft tissue 302 such as skin or gums, and one or more screws 306 may be used to further secure the guide 300 to the underlying bone 304. It will be appreciated that, while introduced in the context of a prior art drill guide, bone and soft tissue support may also be used with the drill guides described below.

Returning to FIG. 1, the teeth 104 (directly beneath the surgical guide 101 and/or support structure 102 in FIG. 1) may be any human or animal dentition. In a dental application, the soft tissue 106 may, for example include gums, gingiva, mucosa, and/or skin, as well as combinations of these. The bone 108 may include a jawbone. It will be understood that the teeth 104, bone 108 and soft tissue 106 are depicted in the generalized form of a dental model, and that the shape of these features in vivo may vary significantly from this abstract representation. In practice, while the device 100 might be test-fitted to such a dental model, the device 100 is intended for use in vivo where an opposing arch, tongue, lips, and other anatomical features and the like are also present.

One or more holes 110 may be provided within the surgical guide 101 that are shaped, sized, and oriented to align a drill, hand cutting tool, or other tool or item with the axial trajectory 112. Further, while the device 100 may be specifically designed and used to guide a drill, it will be understood that any object may be usefully aligned with the device 100 such as a grinding bit, a drill, a surgical drill, a surgical hand tool (or any other surgical tool), a dental implant screw, a healing abutment, an implant, and so forth. It will be noted that in the prior art device 100 of FIG. 1, the hole(s) 110 are relatively deep, and as a result the elongated cylindrical interior shape of the hole(s) 110 fully constrains a drill of matched diameter (usually very slightly smaller than the hole(s) 110) to the axial trajectory 112, and does not permit excursions of such a drill positioned in the device 100 away from the axial trajectory 112 along the length of the drill. Even with smaller drills, the hole(s) 110 may tend to bind a drill that is misaligned to the axial trajectory 112 during use.

While three holes 110 are depicted, it will be understood that the surgical guide 101 may include fewer or more holes. Thus for example, the surgical guide 101 may include one hole, two holes, three holes, four holes, or any other suitable number of holes, such as for multiple implants that are planned for a patient using the device 100. It will also be appreciated that each hole 110 may include a sleeve 114 therein that protects the surgical guide 101 against a cutting edge of a drill or other tool. The sleeve 114 may be formed of a steel, a titanium, a glass, a plastic, an aluminum, or any other material or combination of materials suitably hardened to resist cutting or abrasion from a cutting tool such as a drill.

The axial trajectory 112 may be determined using any suitable computerized or manual case planning tools. For example a dental surgeon may use implant planning software or the like based upon three-dimensional tomographic data or other topology information to determine an appropriate axial trajectory to drill a hole into which a dental implant is to be placed. This surgical plan may be transferred to a patient by fabricating a device, such as any of the devices described herein, that is fitted to a patient's mouth and that includes one or more holes that enforce the axial trajectory.

When placed for use at a surgical site in the patient's mouth (e.g., aligned and fitted to gums, teeth, and so forth), the device may be used to assist a surgeon in creating a properly positioned and oriented hole for placement of the implant. It will be understood that the devices herein are sometimes described in terms of the context in which they are deployed, e.g., placed for use at a surgical site. This may include references to the bone, teeth, and/or soft tissue and so forth that position and support a guide, as well as the target surface where a hole is to be made. While this associated physical context may affect the shape or configuration of a guide, these items are not to be construed as features of the disclosed invention unless otherwise clearly stated to the contrary.

As a significant disadvantage, a surgical drill must be inserted into the device 100 of FIG. 1 on-axis, that is, pre-aligned with the axial trajectory 112, which may prove difficult in confined spaces such as in patients with limited mouth opening and/or in the posterior portions of an arch where the teeth or other anatomy of an opposing arch afford little maneuvering room. In addition, a drill may bind if misaligned in a long tube, even where the drill has a substantially smaller diameter than the guide. As another disadvantage, the device 100 may obstruct a surgeon's view of the location where a drill intersects the target surface, which may prevent the surgeon from viewing drill depth or other aspects of a procedure. Improved drill guides, and methods of using same, are now discussed in greater detail.

Figure 4:
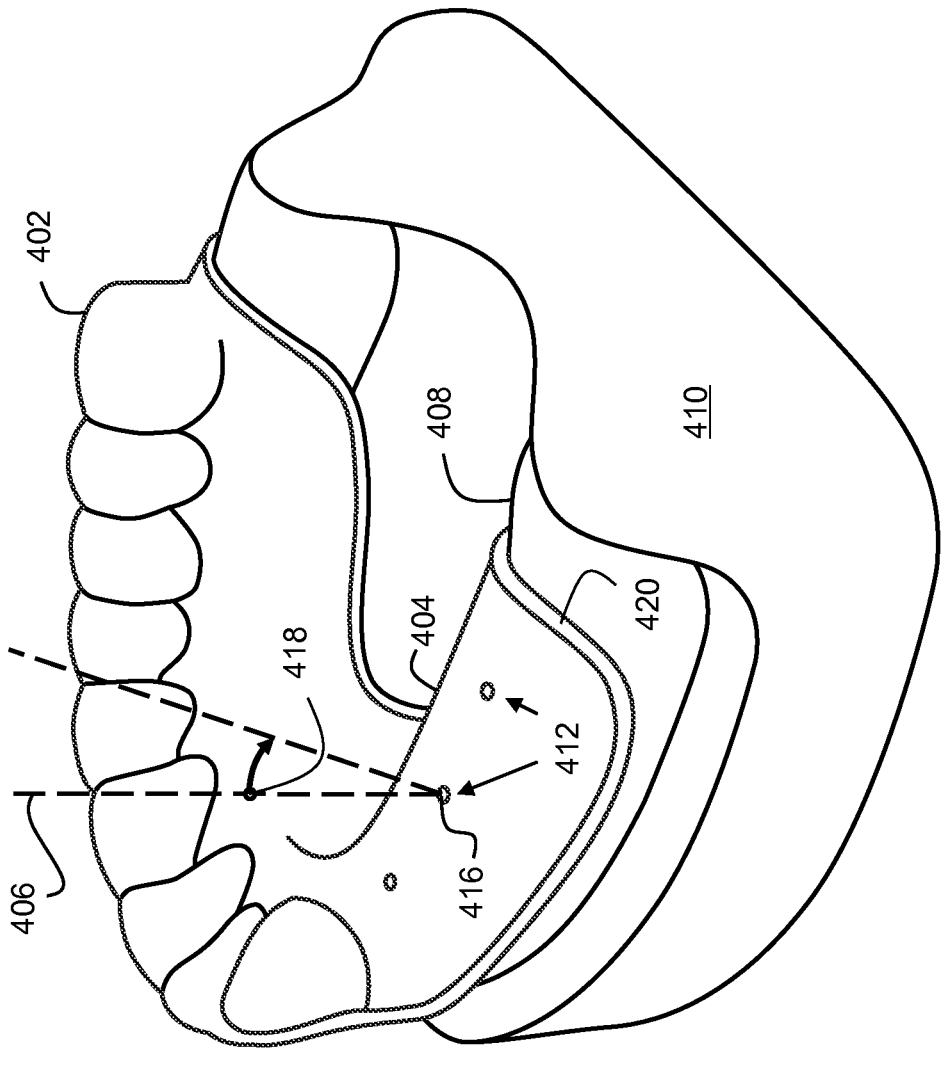
FIG. 4 shows a surgical guide.

FIG. 4 shows a surgical guide. In general, the device 400 includes a support 402 and a surgical guide 404, which may include any of the supports and surgical guides described above, with differences as noted in the following description.

The device 400 may be fabricated using any of a variety of techniques, including casting or molding the device 400 from a model of the patient's mouth. The device 400 may also or instead be fabricated based upon three-dimensional data, along with any suitable rapid prototyping system(s) including without limitation three-dimensional printing, stereolithography, computerized milling and so forth. More generally any computer-driven fabrication technique may be employed including computerized milling, machining, drilling, and so forth. A digital model of the device 400 may be manipulated in a computer environment before fabrication in order to add holes, alignment marks, or other markings such as patient identification data and so forth.

Three-dimensional data may take a variety of forms (e.g., surface, volumetric, etc.) and may be obtained from a variety of imaging techniques. Thus for example, in various uses described herein, three-dimensional data may be 602 obtained, e.g., using any of a variety of three-dimensional surface scanning technologies such as image-based, video-based, structured-light, time-of-flight, or other techniques. Non-surface data may also be obtained, such as interior data characterizing structures below the surface, such as data obtained from CT scans, x-ray tomography, and so forth. In general, as used herein, data beneath a surface will be understood to refer to such interior, volumetric, or non-surface data (which may of course extend up to and include a surface), without regard to the relative orientation of the surface and the interior in general three-dimensional space. It will further be appreciated that surface data and interior data may be registered to provide a digital model with both surface data and interior data. More generally, any form of three-dimensional data that characterizes the relevant surfaces and structures for the design and fabrication of drill guides may be suitably adapted to use with the systems and methods described herein. In addition, dental structures characterized by such three-dimensional models may include any anatomic structure associated with a drilling procedure including without limitation teeth, jawbones, maxillary sinus, nerve canals, and so forth.

In general, the support 402 secures the surgical guide 404 in relation to a location where an axial trajectory 406 meets a target surface 408. The support 402 may include any of the supports described above including a tooth support, a bone support, a soft tissue support, or any combination of the foregoing. While the axial trajectory 406 is depicted as substantially normal to the target surface 408, it will be understood that the axial trajectory 406 may have any suitable orientation and position for forming a desired hole in the bone 410 for a dental implant.

The surgical guide 404 may include one or more holes 412 in a layer 420 to align a tool to the axial trajectory 406 at a first point 416 along the axial trajectory 406 while permitting movement of the tool away from the axial trajectory 406 at a second point 418 along the axial trajectory 406, as indicated generally by an arrow that depicts a possible excursion from the axial trajectory 406 at the second point 418. In general, the surgical guide 404 is formed of a layer 420 of any suitable material or combination of materials. It will be noted in a comparison to the prior art surgical guide 101 of FIG. 1 that the surgical guide 404 disclosed herein uses a thin layer. The hole 412 in the thin-layer guide serves to retain a drill or other device of corresponding diameter (usually slightly smaller in diameter than the hole) in a position centered on the axial trajectory 406 at the first point 416 without constraining axial rotation of the drill at positions away from the first point 416, such as the second point 418. As will be discussed in greater detail below, a second guide may serve to define another point along the axial trajectory 406, such as the second point 418 or any other point spaced away from the target surface 408, and may be used in conjunction with the surgical guide 404 to impose a fixed position and orientation on a drill corresponding to an axial trajectory from a surgical plan. Thus the layer 420 should be sufficiently thin to permit axial movement of a matched drill at points away from the first point 416, while being sufficiently thick to provide strength and rigidity that helps to retain a drill bit centered on the first point 416 during a drilling operation.

It should be clear from the foregoing that a specific thickness of the layer 420 is not required to permit substantial off-axis movement of a tool that is substantially matched (e.g., having a slightly smaller diameter) in size to the hole 412. For example the layer 420 may have a thickness in an area about the hole 412 that is less than a diameter of the hole 412, or less than a radius of the hole 412 (e.g., a one millimeter diameter hole in a 0.5 millimeter layer), or significantly less than a radius of the hole 412 (e.g., a two millimeter hole in a 0.5 millimeter layer). This property of off-axis movement may also be characterized in terms of the degree of off-axis maneuverability afforded to a tool that is substantially matched to the hole 412 (that is, having the same nominal diameter, although the tool necessarily has a slightly smaller diameter if it is not intended to cut the surgical guide 404 during use). For example, the surgical guide 404 may permit a five degree off-axis excursion of a one millimeter diameter drill placed in a one millimeter diameter hole, a ten degree excursion of a one millimeter diameter drill placed in a one millimeter diameter hole, and so forth (generally without damaging or otherwise compromising the guide). It will further be understood that a thickness of the surgical guide 404 may be varied according to other factors such as the type of material used to form the layer 420, the degree of flexibility desired for orientation of a drill about the axial trajectory 406, whether the layer 420 is intended to be cuttable for intra-operative modifications to the axial trajectory 406, the type of drill or tool used, and so forth. All such variations are intended to fall within this disclosure, and may be readily distinguished from the surgical guides of the prior art which purposefully and strictly constrain the position and orientation of a matched drill bit along its entire length to the axial trajectory 406.

As depicted in FIG. 4, the layer 420 may contact the target surface 408 in an area such as the surface area, volume or other space surrounding the hole(s) 412. This configuration may, for example, be useful for positioning an initial pilot hole or the like according to the axial trajectory 406. In other embodiments described below, the layer 420 may be spaced apart from the target surface in an area surrounding the hole, such as to impose the second point 418 of the axial trajectory 406 onto a drill bit or other tool with which the surgical guide 404 is used.

While a single axial trajectory 406 is depicted, it will be understood that the surgical guide 404 may include a plurality of holes 412 for a plurality of axial trajectories 406. The hole(s) 412 may be sized for a drill of a particular diameter, or the hole(s) 412 may be sized for a thin, sharp instrument that can be used to create a bleeding point or other mark at the first point 416 to assist a surgeon in creating an initial pilot hole or the like. The surgical guide 404 may also or instead include a visible marking such as an 'x' or any other suitable marking(s) and/or surface features to mechanically and/or visually guide a surgeon to a correct starting location for a drill. It will be appreciated that the bleeding point may also be established using a prior art tube-type guide or any other technique, without departing from the scope of this disclosure.

The first point 416 may be at a location where the axial trajectory 406 intersects the target surface 408. This location may, for example, include a dental implant site as generally depicted in FIG. 4, and the axial trajectory 406 may be a trajectory of a surgical drill into the dental implant site. More generally, the location may be any surgical site, and the axial trajectory 406 may be a trajectory of a surgical drill into the surgical site. Still more generally, the principles disclosed herein may be applied in any context, surgical or otherwise, where constraints such as maneuvering room, visibility, and flexibility can be usefully addressed with the methods and systems disclosed herein.

In one aspect, the support 402 and/or the surgical guide 404 may be fabricated from a clear plastic or other transparent or translucent material that permits a surgeon to view the target surface 408 and/or surrounding areas during a procedure. The support 402 and/or the surgical guide 404 may be formed of a cuttable material to permit customization of the device 400, such as according to a surgical plan that has been revised after fabrication of the device 400. Where the device 400 is fabricated from a cuttable material, the axial trajectory can be modified, for example, by enlarging the hole with a drill or any other hand cutting tool or powered cutting tool. In other embodiments, each hole 412 may include a hardened ring of stainless steel or any other cut-resistant, biocompatible material such as the materials identified above to provide an abrasion-resistant sleeve. A variety of cuttable, cut-resistant, biocompatible, and/or clear materials are known in the art and may be suitably adapted to use with the systems and methods disclosed herein.

Figure 5:
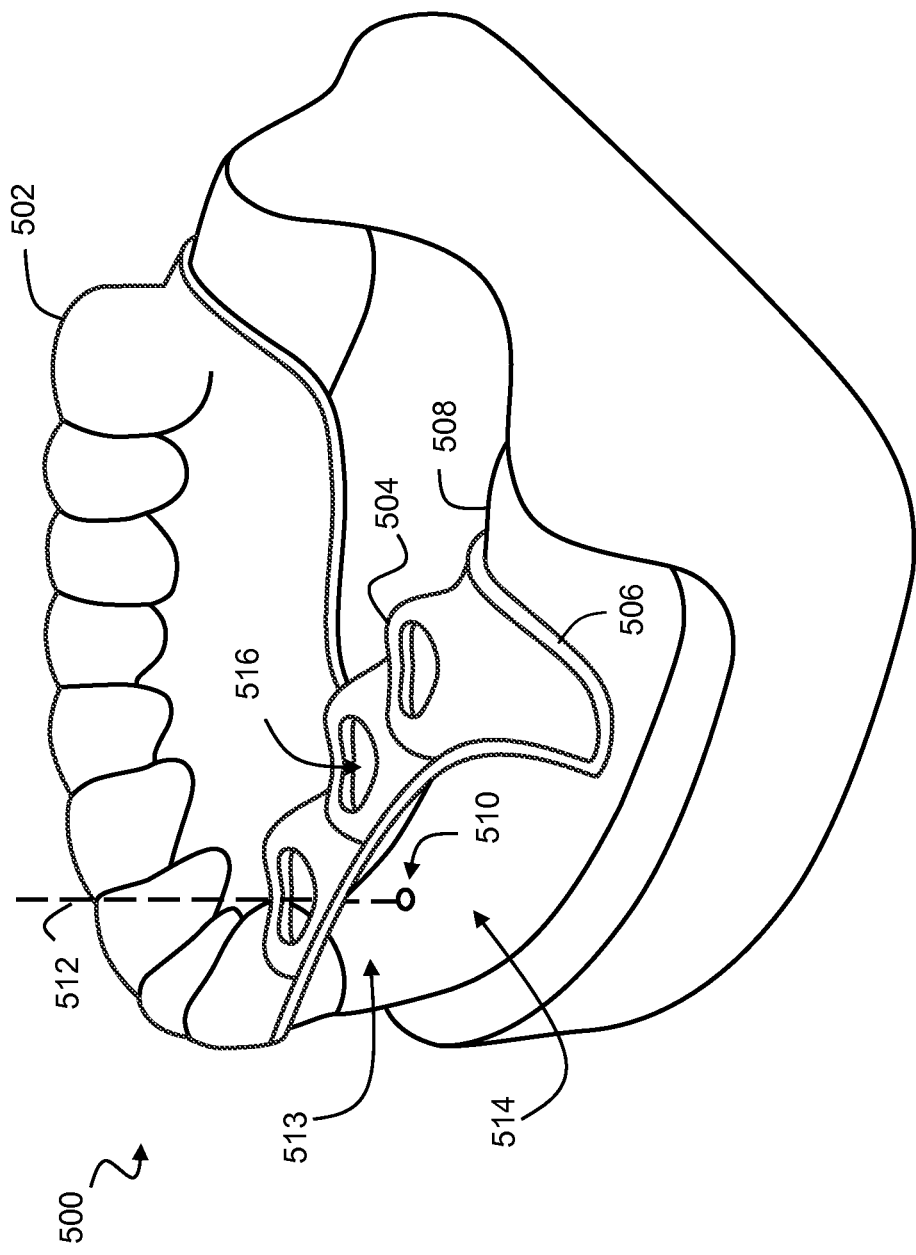
FIG. 5 shows a surgical guide.

FIG. 5 shows a device 500 including a support 502 and a surgical guide 504. The support 502 and the surgical guide 504 may, for example, be as shown and described with reference to FIG. 4, with differences noted below.

A layer 506 of material that forms the surgical guide 504 may be spaced apart from a target surface 508 in an area 510 where an axial trajectory 512 intersects the target surface 508, which area 510 may include any surrounding surfaces and/or volume. The layer 506 may be of any shape or size consistent with adequate support of the surgical guide 504 in a manner to retain a drill or other tool as described herein. In one aspect, the separation of the layer 506 from the target surface 508 provides an interior space 513 around the axial trajectory 512 including a working volume that permits an insertion of a tool off-axis from the axial trajectory 512. In addition, the layer 506 may be shaped to include a window 514 with an opening for physical access to the space between the layer 506 and the target surface 508. This window 514 may be used for access by a surgeon to the target surface 508 for cleaning, inspection, irrigation, suction, material or tool removal, or any other purpose. The window 514 may also or instead provide an opening for visual inspection of the target surface 508 while the surgical guide 504 is in use (e.g., with a drill inserted into one of the holes in the surgical guide 504). The window 514 may include an opening for visual inspection along some or all of the axial trajectory 512 in the space between the target surface 508 and the layer 506 of material. It will be understood that the window 514 or portions thereof may be formed of a clear material that provides visual access into areas enclosed by the surgical guide 504 and/or the support 502 without affording physical access.

A hole 516 in the surgical guide 504 can serve to guide or otherwise retain a tool (not shown) at a point above or otherwise separated from the target surface 508. By using the device of FIG. 5 in combination with (e.g., sequentially with) the device of FIG. 4, the entire axial trajectory 512 of a surgical plan can be enforced by using a first guide (such as the guide of FIG. 4) to establish a point where the axial trajectory 512 intersects the target surface 508 and using a second guide (such as the guide of FIG. 5) to establish a second point along the axial trajectory 512. By guiding a drill through the second guide into the drill hole formed using the first guide, two points sufficient to establish the axial trajectory 512 are imposed on a drill. Where a surgeon wishes to make intra-operative modifications to the axial trajectory 512, the first guide or the second guide may be modified by cutting or otherwise enlarging or re-shaping the hole to shift or re-orient the axial trajectory 512 at the first point, the second point, or both. Similarly, a bleeding point may be used to visually establish one point along the axial trajectory 512 on the target surface 508, and the guide of FIG. 5 may be used to establish another point along the axial trajectory 512. Either the bleeding point or the hole may be modified intra-operatively as desired by the surgeon.

While each hole 516 is depicted as round, any regular or irregular, polygonal or curvilinear, or other shape, or any combination of the foregoing, may also or instead be employed. Thus for example, one or more of the holes 516 may be a square, a hexagon, or other shape capable of retaining a substantially cylindrical drilling tool such as a drill or the like along a path defined by the axial trajectory 512. In another aspect, the holes 516 may be rectangular (or any other shape with a pair of long, parallel sides), thus permitting movement of the axis of a tool in a single plane, e.g., for off-axis insertion of a drill or for manual, intraoperative adjustments to the axial trajectory 512. In such embodiments, alignment marks may be provided to indicate a desired orientation within the plane for the axial trajectory 512.

Numerous variations to the device 500 are possible. For example, the device 500 may include any number of holes 516 for any number of axial trajectories 512. In one aspect, each hole 516 may have a funnel-shaped interior wall as described in greater detail below. It will also be understood that the guide 504 and support 502 may have a variety of physical shapes and configurations without departing from the scope of this disclosure. For example, while the device 500 is depicted as resting on a distal or posterior region of the target surface 508, this supporting structure may be removed, such as to provide a greater working volume for off-axis insertion of a drill into one of the holes 516 in the posterior region.

It will be further understood that a number of devices may be provided having progressively larger hole sizes for progressively larger drills, such as a narrow guide for a pilot hole and a larger guide for a final hole, as well as any number of intervening sizes consistent with a particular cutting operation. In another aspect, a first guide with a small diameter (e.g., 0.7 millimeters for creation of a bleeding point or two millimeters for creation of a pilot hole) may be provided that rests on the target surface 508 where the axial trajectory 512 intersects the target surface 508, and a second guide with a larger hole (e.g., 5.5 millimeters for a final, largest drill size) may be provided that is spaced away from the target surface 508. A narrow diameter pilot drill may be placed into the hole 516 in the second guide and maneuvered into the pilot hole or bleeding point previously created. This second guide may include visual markers to assist a user in centering the pilot drill and a series of progressively larger drills until a final hole diameter is achieved. In another aspect, this may include two or more of the device 400 depicted in FIG. 4 and two or more of the device 500 depicted in FIG. 5. Thus in one aspect there is disclosed herein a plurality of devices each including a hole positioned to align one of a number of progressively larger diameter drills to a first point (which may be a point on the target surface 508 or a point away from the target surface 508) on the axial trajectory 512. In another aspect, the plurality of devices may include holes to align drills to a number of different points on the axial trajectory 512, and/or holes to align drills to a number of different axial trajectories.

Figure 6:
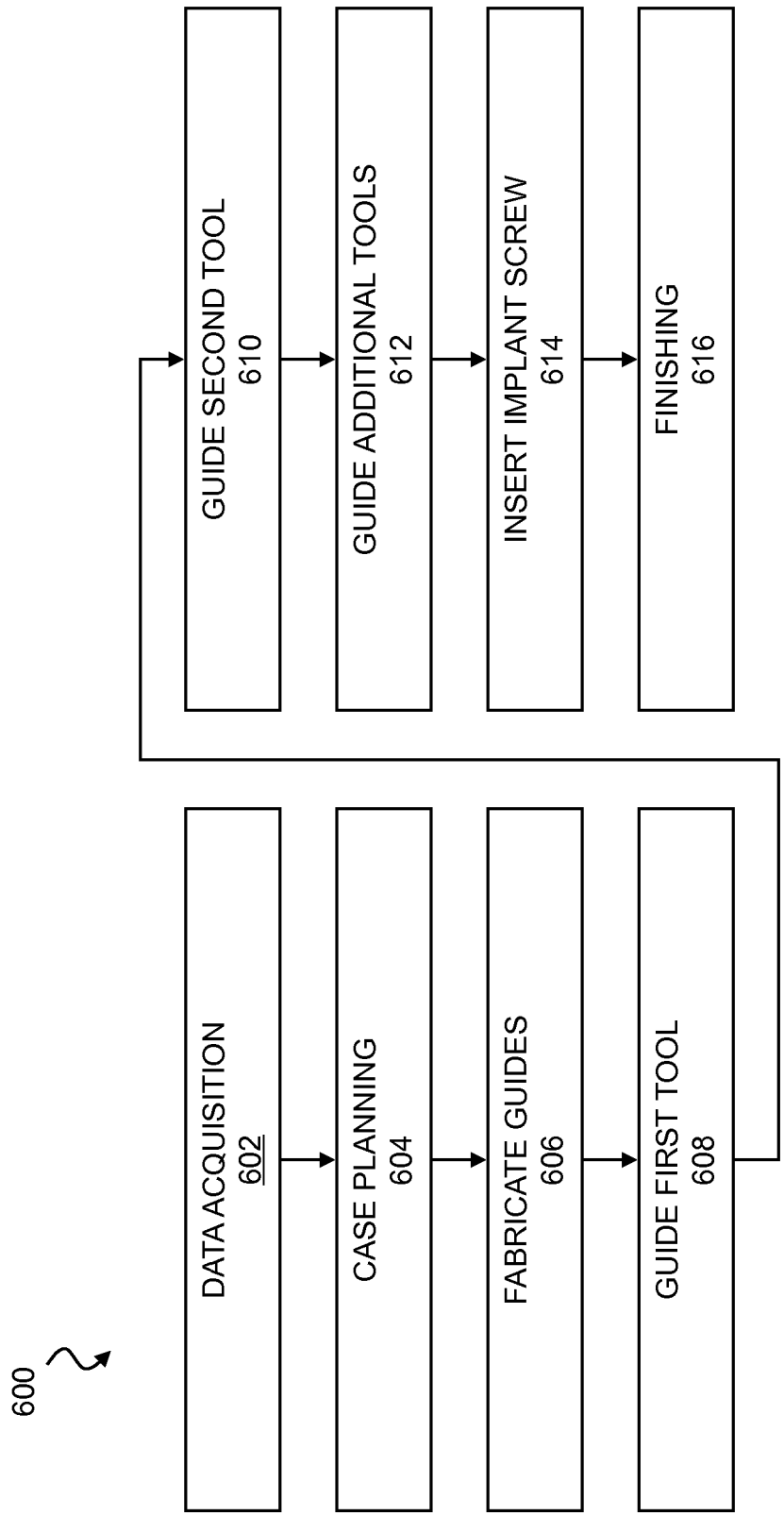
FIG. 6 shows a method for performing a dental implant procedure.

FIG. 6 shows a method for performing a dental implant procedure using the surgical guides described herein. More generally, the following method 600 realizes an axial trajectory of a cutting process, which may be usefully employed in a dental implant procedure, or any other surgical procedure that includes translating an axial trajectory from a surgical plan to a patient. Still more generally, the method 600 may be usefully employed in any context where an axial trajectory is transposed from a model to a physical object.

As shown in step 602, the method 600 may begin with data acquisition. This may include acquisition of three-dimensional data from beneath a surface of a surgical site, such as interior data obtained from within one or more dental structures (e.g., teeth, bone, soft tissue, etc.) through x-ray tomography or any other suitable subsurface imaging technology. This may also or instead include an acquisition of three-dimensional surface data obtained using any suitable surface scanning technology. This may also or instead include an acquisition of two-dimensional radiographs such as orthopantomographs or periapicals. This may also include an acquisition of three-dimensional information in the form of physical models such as casts, molds, or impressions representative of a dental implant site and surrounding dentition, tissue, and the like.

Thus it will be understood that data acquisition may take a variety of forms. Data acquisition may include acquisition of a physical or analog model of a surgical site and/or teeth using, e.g., conventional dental impressioning to create a physical model and/or a cast for same. Data acquisition may also or instead include a three-dimensional surface scan (using, e.g., video-based techniques, structured light techniques, or any other suitable three-dimensional surface scanning techniques) of a surgical site, or of a physical model produced from a dental impression, or of interior surfaces of a cast for a physical model. Data acquisition may also or instead include an x-ray tomographic scan or surface scan of an acrylic shell or other vacuum-formed or similar thin layer cast of a physical model or surgical site. Data acquisition may also include a capture of supplemental data such as prescription information derived from a patient interview, questionnaire, or the like, or information received from another treating physician.

As shown in step 604, the method 600 may include case planning to determine a course of action for a dental procedure. In the case of a dental implant, this may include selecting a suitable implant and determining an axial trajectory for a hole to receive an implant, or the like. In general, positioning of the axial trajectory is influenced by a variety of factors such as the position, shape, and size of teeth, the avoidance of vital structures, and the existence of adequate bone volume around the hole. Depending on the procedure, the axial trajectory may be realized using any number of drills (e.g., one to seven) of increasing size from a smallest size for a pilot hole to a largest size for the final hole that will receive the implant. Case planning may also include an identification of other pre-surgical treatment(s) in preparation for an implant. Case planning may include the use of case planning software, including any of a variety of commercially available software tools, to assist in assessment of a surgical site and three-dimensional positioning and orientation of an axial trajectory.

As shown in step 606, the method 600 may include fabricating a number of surgical guides such as any of the guides described herein. This may for example include interim steps such as a creation of stereolithography fabrication files, milling machine instructions, or the like to control a computerized fabrication system including without limitation a stereolithography system, a digital light processing system, a computer-controlled milling machine, a three-dimensional printing system, or any other computer-driven process such as a computer-controlled drill, lathe, and so forth, as well as any combination of the foregoing. This may also include manual fabrication based upon a physical model of a surgical site. For example a material such as any pliable, curable material may be placed on the physical model to capture a complementary shape, and then cured to a sufficient hardness for use as a support structure. Similarly, a sheet of material such as plastic, which may be clear plastic, may be formed to the physical model using vacuum forming or the like to produce the support structure. In one aspect, fabrication may include a combination of manual and automated steps. It will also be appreciated that fabrication as contemplated herein may include any number of interim fabrication and data acquisition steps, such as fabricating an arch model using stereolithography (or any other suitable technique for converting a digital model into a physical model), and using the physical arch model for subsequent scanning or fabrication steps such as preparing a shell that will be further processed to fabricate a drill guide.

For example, a thin-layer guide such as various guides described above may be fabricated from a plaster model or the like to provide a form for a tooth support. The resulting cast may form a shell that maps the contours of a surgical site in a physical form. The shell may then be subjected to further computerized processing to provide a surgical guide. For example, an axial trajectory determined using three-dimensional data and case planning software may be mapped to the manually fabricated support structure or shell and used with a computer-controlled milling machine or the like to accurately position and create a hole for a surgical guide in the support. In another aspect, fabricating the surgical guide(s) may include fabricating the shell or support with an automated fabrication process and subsequently milling the hole(s) with a manual or automated milling process or the like. In general, creating a hole with a computer-controlled machine as described herein may include any suitable computer-controlled apparatus, such as a computer-controlled milling machine, a computer-controlled drilling machine, a hole punch, a heated probe (where the support is formed of a meltable plastic or similar material), or any other machine that can be programmed or operated with a computer to place a hole with a desired size in a desired location.

As shown in step 608, the method 600 may include guiding a first cutting tool with a first guide, such as any of the surgical guides described herein. This may include guiding the first cutting tool at a first point along the axial trajectory where the axial trajectory intersects a target surface while permitting movement of the first cutting tool away from the axial trajectory at one or more other points along the axial trajectory. The first cutting tool may, for example, be a surgical drill. In another aspect, the first cutting tool may be a hand dental tool such as an osteotome or other tool used to manually bore a hole for a dental implant. As another example, the first cutting tool may be a sharp, pointed hand tool used to create a bleeding point at a desired location. More generally, the first cutting tool may include a drill, a surgical drill, a rotary tool, a surgical hand tool, or any other tool that might be guided along an axial trajectory. The target surface may be a dental implant site, or more generally any surgical site.

As shown in step 610, the method 600 may include guiding a second cutting tool with a second guide such as any of the surgical guides described herein. This may include guiding the second cutting tool at a second point along the axial trajectory spaced apart from the target surface while permitting movement of the second cutting tool away from the axial trajectory at the one or more other points along the axial trajectory, such as using one of the thin-layer guides described above. The first cutting tool may be the same as the second cutting tool, such as where guides are sequentially applied to establish a point on the target surface and then a point away from the target surface for a particular drill. Or the first cutting tool and the second cutting tool may be different cutting tools. For example, the second cutting tool may have a larger diameter than the first cutting tool, such as with a series of progressively larger cutting tools that result in a final hole size suitable for a dental implant (or other implant anchor or the like). In another aspect, the second guide may be used to guide a plurality of progressively larger diameter drills. This may be suitable where, for example, the first guide centers a pilot hole or a bleeding point, and the hole in the second guide is over-sized relative to the pilot hole or bleeding point, but may nonetheless enforce the desired axial trajectory on a final drill matched to the size of the hole in the second guide. In this example, a dentist or surgeon may insert the smaller drill into the hole in the second guide and maneuver the tip of the drill into the pilot hole or bleeding point and center the smaller drill in the second guide by eyesight, or with the aid of visual alignment marks or the like on the second guide, aligning the drill with the axial trajectory. In general, the second cutting tool may include a drill, a surgical drill, a rotary tool, a surgical hand tool, or any other tool that might be guided along an axial trajectory.

In one aspect, the first guide and the second guide may be separate guides as generally discussed above. In another aspect, the first guide and the second guide may be integrated into a single physical device such as the two-layer device described below.

As shown in step 612, the method 600 may optionally include providing and using a plurality of guides with a respective plurality of progressively larger holes for at least one of the first point and the second point along the axial trajectory. Thus any number of progressively larger drills may be guided with suitably matched surgical guides.

As shown in step 614, after a hole of suitable diameter centered on the axial trajectory has been prepared, a dental implant may be inserted into the resulting hole. This may include, for example, a self-tapping implant screw or any other suitable implant.

As shown in step 616, any number of finishing steps may be performed including steps performed immediately after placement and steps performed at a later time such as steps relating to, e.g., aesthetics and fit of a crown, abutment, or other dental object affixed to an implant.

As described above, the first cutting tool and the second cutting tool may be the same or different, and may include any tool usefully employed by a surgeon including without limitation a drill, a surgical drill, a rotary tool, and a surgical hand tool. The present invention is in no way limited by the type of surgical tools or instruments employed. Additionally, as noted above, the guides or guide layers employed may include any of the surgical guides and/or supports described herein. More generally, the order in which the steps of the present method are performed is purely illustrative in nature, and the individual steps may be re-ordered, removed, supplemented, modified, or otherwise altered without departing from the scope of this disclosure.

For example, in one aspect, a bleeding point may be manually positioned by a surgeon without the assistance of a guide, and the "second guide" described above may be used with the manually positioned bleeding point to align a drill to the axial trajectory. Thus in one aspect there is disclosed herein a method that includes creating a bleeding point at a first point on a target surface and guiding a drill with a guide that includes a hole spaced away from the target surface. The guide may include a thin layer guide with a computer-positioned hole that is created using any of the techniques described above.

By way of further example, a variety of combinations of automated and manual steps, and/or combinations of computerized and physical manipulations may be used consistent with the scope of this disclosure. A physical impression may be used to create a shell for a thin layer guide, or the thin layer guide may be fabricated using stereolithography or any other suitable computerized fabrication technique from a digital model that includes the guide holes or a combination of these techniques may be employed. In another aspect, a physical dental model (e.g., from a physical impression) may be scanned to digitize surface data, and this data may be combined with CT scan data to plan a trajectory for a procedure, after which a digital model of a guide including one or more guide holes may be directly fabricated using any suitable computerized fabrication technique. Or a shell for a physical thin layer guide may be obtained from a physical dental model and digitized with any suitable scanning technique such as a surface scanning technique or x-ray tomography to provide a digital model of the shell, and holes may be placed within the shell in a computer modeling environment. In this latter example, the resulting digital drill guide model may be used to place holes in the physical thin layer guide (with a computerized or manual fabrication step), or the digital drill guide model may be used for direct fabrication of an entire, final drill guide. In another aspect, a three-dimensional surface scanning technique may be used to obtain an initial, digital impression of the surgical site (and surrounding dentition), which may in turn be used to fabricate a physical model using any suitable computerized fabrication technique. This physical model may be used in lieu of the physical impression in any of the foregoing procedures. Still more generally, the guides described herein may be fabricated using many combinations of steps with physical and/or digital models, based upon many combinations of source data (e.g., surface scans, CT scans, etc.), and using a variety of computerized and/or manual fabrication techniques. All such combinations that can be used to obtain a physical realization of a guide as described herein are intended to fall within the scope of this disclosure.

By way of further example, a variety of combinations of automated and manual steps, and/or combinations of computerized and physical manipulations may be used consistent with the scope of this disclosure. A physical impression may be used to create a shell for a thin layer guide, or the thin layer guide may be fabricated using stereolithography or any other suitable computerized fabrication technique from a digital model that includes the guide holes, or a combination of these techniques may be employed. In another aspect, a physical dental model (e.g., from a physical impression) may be scanned to digitize surface data, and this data may be combined with CT scan data to plan a trajectory for a procedure, after which a digital model of a guide including one or more guide holes may be directly fabricated using any suitable computerized fabrication technique. In another aspect, a shell may be obtained from a physical dental model, and the shell may be digitized using any suitable three-dimensional scanning technique such as a three-dimensional surface scan or x-ray tomography to provide a digital model of the shell, and holes may be placed within the digital model of the shell in a computer modeling environment to provide a digital drill guide model. A physical drill guide may then be fabricated from the digital drill guide model using stereolithography or any other suitable rapid prototyping or fabrication technique. The digital drill guide model may also or instead by used to control an automated drilling machine to place holes in the shell, thus converting the shell into a thin layer guide as described above.

In another aspect, a three-dimensional surface scanning technique may be used to obtain an initial, digital impression of the surgical site (and/or surrounding dentition), which may in turn be used to fabricate a physical model using any suitable computerized fabrication technique. This physical model may be used in lieu of the physical impression in any of the foregoing procedures. Still more generally, the guides described herein may be fabricated using many combinations of steps with physical and/or digital models, based upon many combinations of source data (e.g., surface scans, CT scans, etc.), and using a variety of computerized and/or manual fabrication techniques. All such combinations that can be used to obtain a physical realization of a guide as described herein are intended to fall within the scope of this disclosure.

More generally, numerous methods may be employed for fabricating surgical guides as described herein. By way of further illustrative example, and not by way of limitation, a number of additional, specific methods are now described. In one embodiment, three-dimensional data may be obtained from a patient's dental arch with a physical dental impression, which may in turn be used to fabricate a physical model of the arch. An acrylic sheet or the like may then be formed onto the physical model to obtain a shell. The shell may then be used to fabricate a radiographic stent that includes a radiopaque marker of the future tooth position and one or more fiduciary markers (e.g., three fiduciary markers). Three-dimensional x-ray tomography data may then be obtained directly from the patient while the patient is wearing the radiographic stent (e.g., the shell with the fiduciary markers). Three-dimensional x-ray tomography data may also be obtained from the radiographic stent alone (e.g., without the patient's dentition) to provide source data for the drill guide. Implant planning software may then be used to determine an implant trajectory to provide implant data, and the implant data may be combined with the three-dimensional data from the radiographic stent alone to provide a digital model. The drill guide may then be fabricated from this three-dimensional data set (the digital model of the drill guide), with any suitable modifications, adaptations, or other processing for output to a stereolithography system or stereolithography design environment. In the stereolithography design environment, which may be conventional stereolithography software or software customized for designing and fabricating drill guides as described herein, implant trajectories in the form of guide holes may be imposed on the digital model based open the implant trajectories. The shell may also be further modified to remove or add to surfaces thereof, such as to provide windows, alignment marks, and so forth, or to remove portions of the shell that are not required for support of the guide or otherwise not desired. The resulting digital model, with any modifications as described above, may then be fabricated using stereolithography or any other suitable fabrication technique.

In another aspect, an initial digital model of a patient's dental arch may be obtained directly from the patient using any suitable three-dimensional surface scanning technique such as video-based scanning, structured light scanning, and so forth. A shell may be created from the initial digital model within a computer design environment, and used to fabricate a shell corresponding to the patient's dental arch with, e.g., stereolithography. The shell may then be used to create a radiographic stent and the method may proceed as described above.

In another aspect, the drill guide may be more generally hand-tooled. For example, three-dimensional surface data may be obtained from a patient's dental arch with a physical dental impression, which may be used in turn to fabricate a physical dental model using known techniques. A shell may be vacuum formed to the physical dental model, and the shell may be used to fabricate a radiographic stent as described above. Three-dimensional data may then be captured of a patient wearing the radiographic stent, and the resulting data set may be used within implant planning software to determine an appropriate implant trajectory. The coordinates that define the implant trajectory may be physically transferred to the shell using any suitable technique, and one or more holes may be manually drilled or otherwise created in the shell to provide a drill guide.

As previously noted, these specific examples are not intended to limit the generality of the invention. Numerous other variations and adaptations to the foregoing are possible, and all such variations that are apparent to one of ordinary skill in the art are intended to fall within the scope of this disclosure.

It will also readily be appreciated that a kit may be provided for a surgical procedure according to any of the foregoing. The kit may, for example, include one or more of the guides described above, such as a number of guides with progressively larger holes for an axial trajectory. The kit may also include a corresponding collection of drills, such as disposable drills, or the holes may be sized for a standard dental or surgical drill set. The kit may also or instead include a number of drill stops to achieve a predetermined drill depth for a particular procedure, or drill stops for a surgeon to variably control depth. In another aspect, the corresponding collection of drills may be fabricated to include a drill stop, such as by manufacturing drill bits with varying diameter sections. The kit may also or instead include a variety of related components, such as written instructions for a procedure, computerized instructions for a procedure (on a compact disk or other storage medium), sterilization materials, dental models, implant screws, and so forth. The kit, or portions thereof, may be packaged in a sterile packaging. More generally, any assembly and packaging of components and materials to accompany the drill guides described herein may usefully be provided as a kit for dental or other surgical use.

Figure 7:
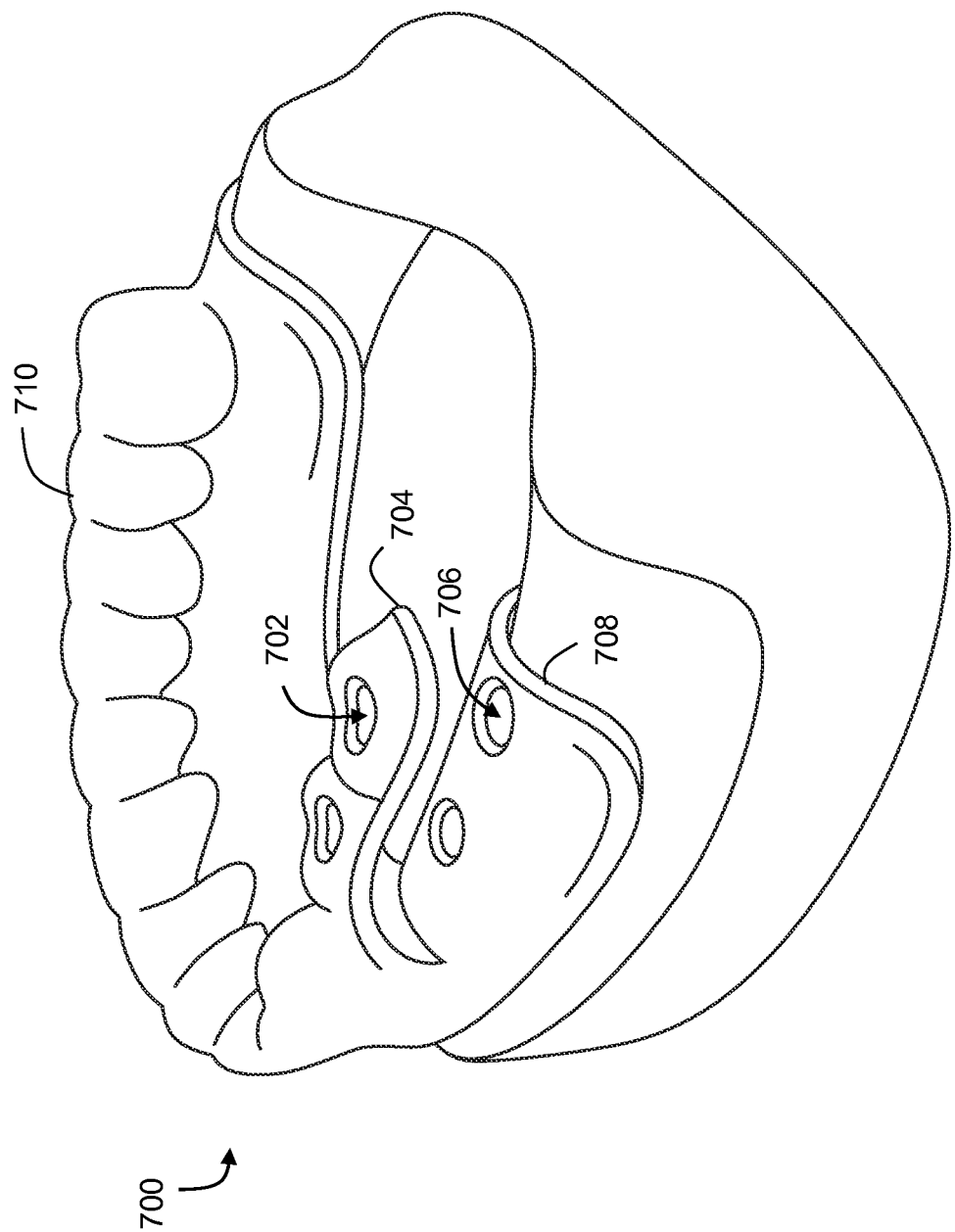
FIG. 7 shows a two-layer surgical guide.

FIG. 7 shows a two-layer surgical guide. As depicted, a device 700, which may include some or all of the features of any of the devices described herein, may include two or more separate layers integrated into a single guide. More specifically, the device 700 may include a first hole 702 in a first layer 704 positioned to align a tool or the like to an axial trajectory at a first point along the axial trajectory and a second hole 706 in a second layer 708 spaced apart from the first layer, the second hole 708 positioned to align the tool to the axial trajectory at a second point along the axial trajectory, all as generally discussed above. More specifically, the first layer 704 may be vertically spaced apart from the second layer 708 along the axial trajectory so that the first hole 702 and the second hole 706 can fully define the axial trajectory as generally described herein. Any number of additional holes for additional axial trajectories may also be included. The device 700 may include a support 710, such as any of the supports described above, to secure the surgical guide in relation to a location where the axial trajectory meets a target surface of a surgical site. As depicted, the first layer 704 may be attached to the support 710 on a single end thereof to provide full physical and visual access to the surgical site and surrounding areas. In another aspect, a second end of the first layer 704 may include a further support structure attached to the second layer, such as along a rear edge of the layers, for additional structure support and rigidity. In another aspect, the device 700 may include side walls between the first layer 704 and the second layer 708 fully or partially enclosing a space between the two layers. More generally, a variety of supporting configurations and structures may be included in the device 700, and all such variations are intended to fall within the scope of this disclosure.

The first hole 702 may have the same diameter as the second hole 706. In other embodiments, the second hole 706 may have a smaller diameter than the first hole 702 (or alternatively stated, the first hole 702 may have a larger diameter than the second hole 706) so that, for example, a drill stop or the like may be used with a drill, where the drill stop is sized to fit through the first hole 702 but not through the second hole 706. The first layer 704 and the second layer 708 may be sufficiently spaced apart to provide a space for an insertion of a tool into the first hole 702 off-axis from the axial trajectory.

In one aspect, the guide may be fabricated using two separate physical models of the surgical site. For example a first model may be obtained with tooth or teeth that are to be replaced by an implant-supported crown. A layer formed on this first model may provide a layer away from the target surface to define a first point along the axial trajectory. A second model may be obtained with the tooth (or teeth) removed so that a layer formed on this model rests directly against the target surface of the surgical site. The first layer may then be molded onto or otherwise attached to the second layer in various support areas to provide a one piece, two layer guide. In another aspect, the entire device 700 may be fabricated from a computerized model or the like as generally discussed above.

Figure 8:
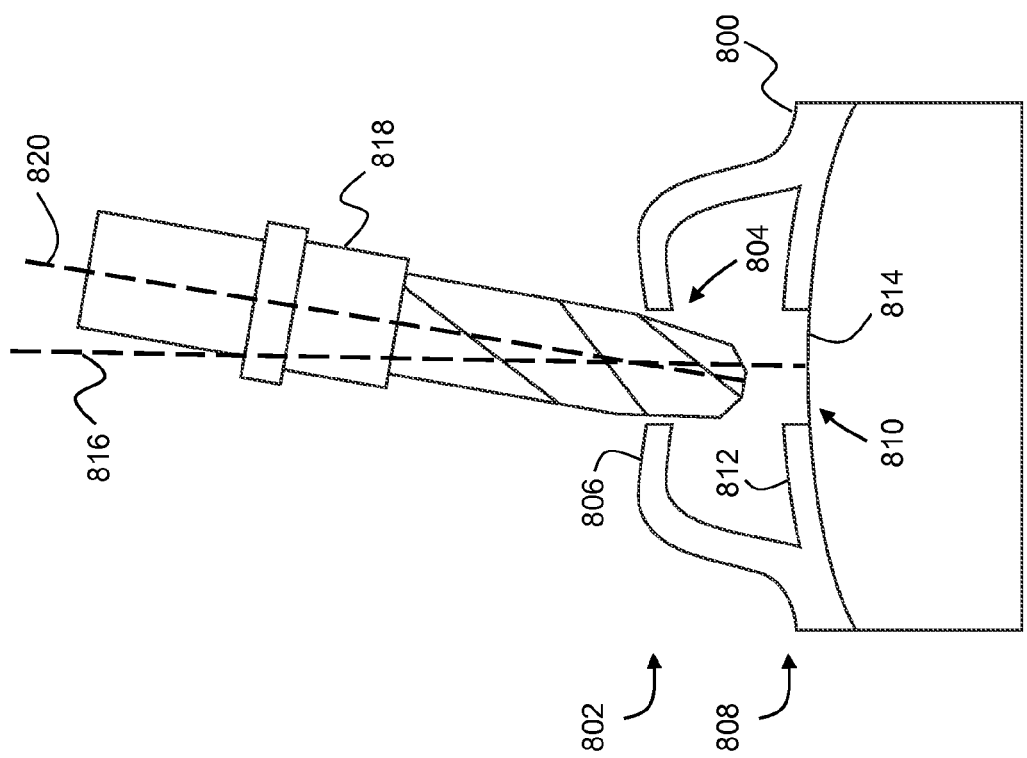
FIG. 8 is a cross-sectional view of a two-layer surgical guide.

FIG. 8 is a cross-sectional view of a two-layer surgical guide. The device 800 may include any of the devices or features described herein. As shown, the device 800 may include a first guide 802 formed by a first hole 804 in a first layer 806 and a second guide 808 formed by a second hole 810 in a second layer 812 which may include any of the guides, holes, and layers described above. The first guide 802 and the second guide 808 may be integrated into a single device to provide a full spatial definition for an axial trajectory 816 for a tool 818. Thus for example, the first guide 802 may align the tool 818 at a point away from a target surface 814 while the second guide 808 may align the tool 818 where the axial trajectory 816 meets the target surface 814.

This arrangement may advantageously reduce the number of separate devices required for a surgical procedure. For example, the device 800 may permit an off-axis insertion of the tool 818 along a second axis 820 as depicted, thus decreasing the intraoral clearance required to insert the tool 818 into the device 800. The space between the first layer 806 and the second layer 812 may also be accessible through a window or the like to provide physical and/or visual access to the surgical site and/or the axial trajectory 816. In general, the device 800 may be formed to rest upon a target surface 814 and provide tooth support, soft tissue support, and/or bone support as generally discussed above. It will be noted that the device 800 is depicted with side walls for support of the first guide 802 that might run along a dental arch, while the device 700 of FIG. 7 provides end support for an upper guide. In general, side walls, end walls, or any other supporting structure(s), as well as combinations of these, may also or instead be employed to secure a guide in a desired location away from a target surface, and all such variations are intended to fall within the scope of this disclosure. It will further be appreciated that, while two side walls are depicted in the cross-sectional view of FIG. 8, a cross section of the guide may include a window or opening on either side or both sides, as shown for example in the figures above. Thus while the first hole 804 and the second hole 810 are generally fixed relative to one another in a two-layer guide, there is no requirement of any particular shape or arrangement of supporting structure(s) used to maintain this spatial relationship unless otherwise explicitly stated to the contrary.

Numerous variations will be readily appreciated. In one aspect, the device 800 may include any number of additional layers, each providing a guide at a different distance from the target surface 814. In another aspect, one or more of the plurality of guides may be formed of a cuttable material while one or more other ones of the plurality of guides may be formed of a cut-resistant material, or include a sleeve or the like to resist cutting. Where a cuttable material is used, the guide(s) may be modified before or during use by cutting or otherwise modifying the hole(s) therein.

Figure 9:
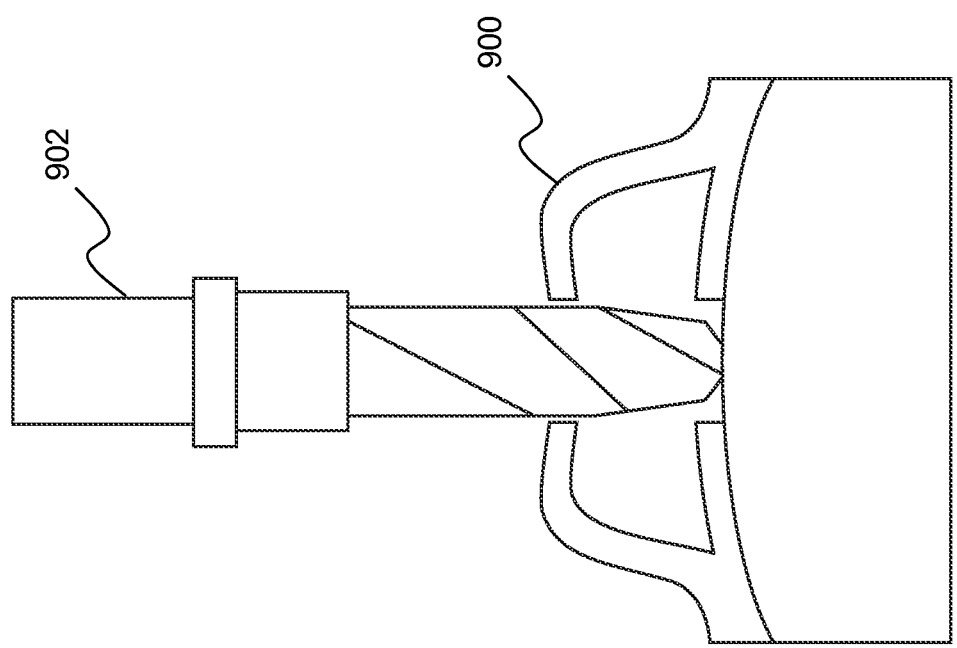
FIG. 9 is a cross-sectional view of a two-layer surgical guide.

FIG. 9 is a cross-sectional view of a two-layer surgical guide. The device 900 may be any of the surgical devices described above, such as the device 800 of FIG. 8. As shown in FIG. 9, after a tool 902 is inserted into a first hole of the device 900 (either on-axis or off-axis), a tip of the tool 902 may be directed toward the second hole, thus bringing the tool into alignment with a desired axial trajectory.

It will be appreciated from the foregoing that a window may be usefully incorporated into a surgical guide for visual and/or physical access to a surgical site. Using a thin-layer construction as described, for example, with reference to FIG. 5, a window may be formed directly in the surgical guide (or the surrounding support) from an opening between the layer and the target surface, or for a two-layer guide, between a first layer and a second layer. For physical access, the window may include a physical opening in the device. For visual access, a clear or transparent region of material may also or instead be used. In another aspect, the entire device 900 may be fabricated of a clear plastic or other transparent material. The window may provide a view of the axial trajectory where the axial trajectory intersects the layer, or anywhere else between the layer and the target surface, and may generally provide for visual access or physical access to the surgical site.

Figure 10:
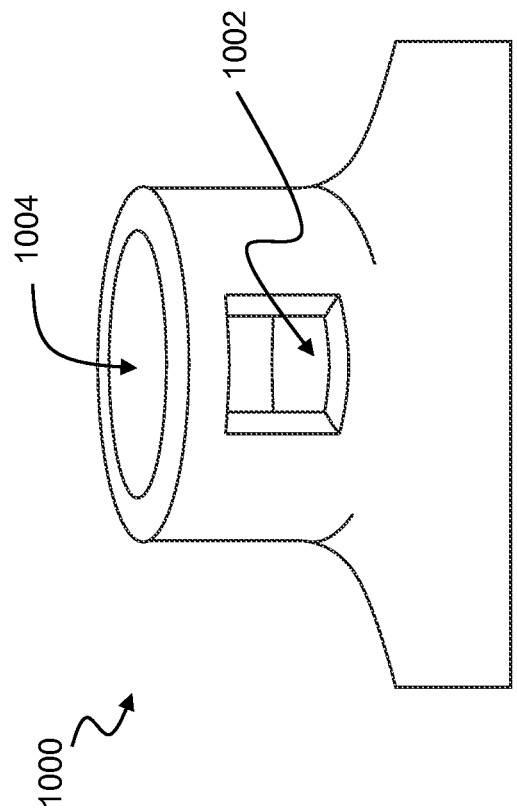
FIG. 10 shows a surgical guide with a window.

FIG. 10 shows a surgical guide with a window. In general, a device 1000 may include a surgical guide and a support as described above. The device 1000 may also include a window 1002 bounded, for example, on four sides by the walls of the surgical guide. The window 1002 may provide a view of the axial trajectory where the axial trajectory intersects the target surface. The window 1002 may also or instead provide a view of any other portions of the axial trajectory, or a drill or other tool inserted into the surgical guide and traveling along the axial trajectory. The window 1002 may be formed with a transparent material in the surgical guide, or the window 1002 may include a physical opening in the surgical guide or the support that provides a view of the space surrounding the axial trajectory as well as physical access to the space. More generally, the window may include any structures and/or materials that provide visual and/or physical access to an interior space 1004 of the device 1000. The interior space

1004 may be coextensive with a hole used to guide a drill, or the interior space 1004 may include additional interior volume(s) of the device 1000, such as regions that accommodate off-axis insertion of a tool as generally discussed above.

Figure 11:
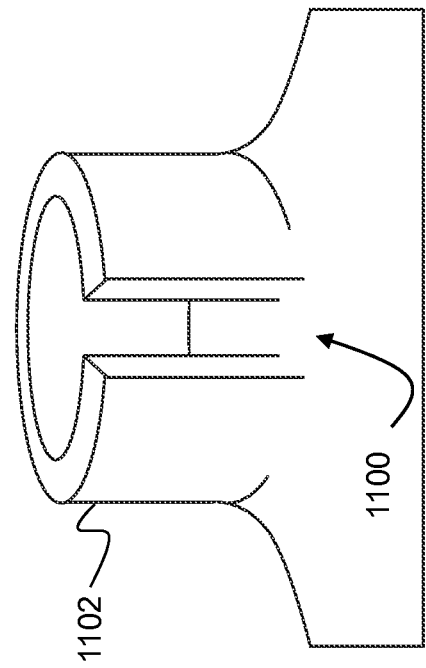
FIG. 11 shows a surgical guide with a window.

FIG. 11 depicts another embodiment of a window 1100 in a surgical guide 1102. As shown in FIG. 11, the window 1100 may be formed from a slit or other opening bounded on two substantially vertical sides by the walls of the surgical guide 1102 (or support). This window 1100 may proceed from a top to a bottom of the surgical guide 1102 or along any other length of the walls. In one aspect, the window 1100 may reach at least to the target surface in order to provide visual inspection of a drill or other tool as it contacts the target surface.

Figure 12:
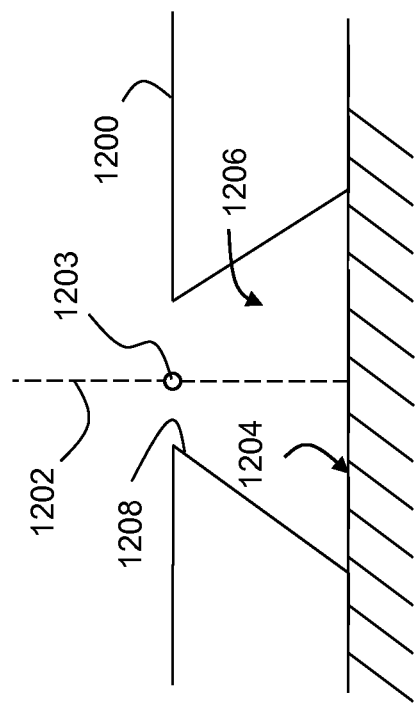
FIG. 12 is a cross-sectional view of a surgical guide.

FIG. 12 is a cross-sectional view of a surgical guide. It will be noted that some of the surgical guides described above are designed to guide a tool or the like at a first point along an axial trajectory while permitting excursions of the tool away from the axial trajectory at other points along the axial trajectory. This feature may be achieved using a thin layer as discussed generally above. In another aspect, this feature may be achieved using a relatively thicker guide (e.g., of a thickness used in prior art drill guides) with a funnel-shaped or similar geometry for a hole in the guide 1200. This geometry may confine a tool (not shown) at one point along the axial trajectory 1202, while permitting excursions such as off-axis insertion or use, at other points. For example, as depicted in FIG. 12, a tool inserted into the guide 1200 may be confined at a point 1203 away from a target surface 1204, but permitted to move away from the axial trajectory at other locations, such as positions closer to (or farther from) the target surface, or more generally to move away from the axial trajectory within a space 1206 within the guide 1200. Thus in one aspect a surgical guide disclosed herein may include a hole that is tapered into a funnel shape. The guide may be thicker than the diameter of the funnel at its narrow end 1208 or, using a different benchmark, thicker than a diameter of a tool matched to the guide 1200. It will be understood that while a linear funnel shape is depicted, any similar shape, such as an arc, a parabola, or any other regular or irregular wall profile that joins a wider hole on one side of the surgical guide to a narrower hole on an opposing side (e.g., a drill entry side and a drill exit side or the like) may be similarly employed without departing from the scope of this disclosure.

Figure 13:
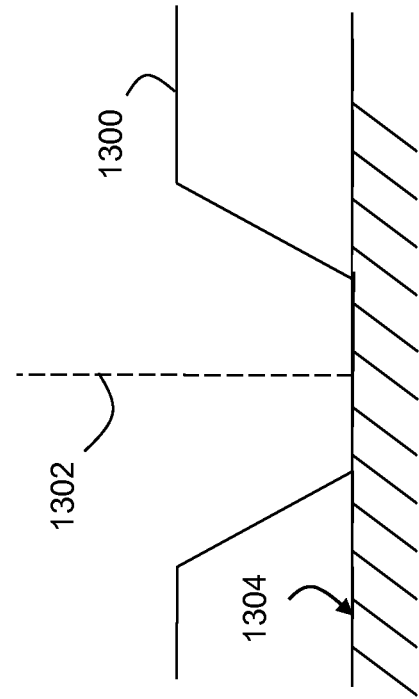
FIG. 13 is a cross-sectional view of a surgical guide.

FIG. 13 is a cross-sectional view of a surgical guide. As with FIG. 12 above, the surgical guide 1300 of FIG. 13 guides a tool at one point along an axial trajectory while permitting movement of the tool at other points along the axial trajectory. More specifically with reference to FIG. 13, the surgical guide 1300 guides a tool of matched diameter where an axial trajectory 1302 intersects a target surface 1304, while permitting excursions of the tool off the axial trajectory 1302 away from the target surface 1304. Numerous similar arrangements will be readily appreciated and are intended to fall within the scope of this disclosure, such as any cross-sectional profile that confines a tool to an axial trajectory at one or more points along the axial trajectory while permitting off-axis movement at other points along the axial trajectory. In other embodiments, a narrowest portion of the hole may be between a top and bottom opening of the surgical guide. So for example, the hole may be wide at a top surface, taper to a narrower diameter in an interior portion of the guide, and then widen again to a relatively wider opening at a bottom surface. Still more generally, any profile for the taper or interior shape of the hole consistent with the uses of a drill guide described herein may be suitably incorporated into the device without departing from the scope of this disclosure.

The funnel shape may also be usefully incorporated into a thin layer guide, such as to steer a tool into a hole or to narrow a layer at the hole to provide greater freedom of off-axis movement for a matched-diameter tool inserted therein. In addition, while the holes described herein may useful employ a linear taper to provide a funnel shape as generally shown and described above, it will be understood that other tapers may also or instead be employed, such as curvilinear tapers or compound tapers that variously increase and decrease as the hole is traversed from a top surface of the layer (e.g., away from the target surface) or a bottom surface (e.g., adjacent to the target surface). Thus the hole may more generally include a tapered wall with a diameter that varies along an axis passing through the hole. The diameter may, for example, vary from a widest diameter on top to a narrowest diameter on the bottom (as in FIG. 13), or the diameter may range from a narrowest diameter on the top to a widest diameter on the bottom (as in FIG. 12). The narrowest diameter may instead be between the top and bottom surfaces of the layer to provide a dual-funnel shape. In another aspect, the narrowest section may extend from within the hole to a bottom surface of the guide. This configuration may be employed in a relatively thick tube guide or the like to accommodate off-axis insertion in a top, open funnel portion of the guide, while providing longer side walls to axially constrain a drill in a lower, cylindrical portion of the guide. Thus more generally a variety of shapes for the hole may be provided that vary from a narrowest diameter section (to guide a drill) and wider diameter sections (to accommodate off-axis movement of the drill when the guide is in use), and all such variations are intended to fall within the scope of this disclosure.

In this context, the "shape" refers to the cross-sectional, vertical profile as depicted in FIGS. 12 & 13. Each hole also has a z-axis shape, e.g., a cross-sectional, horizontal profile, as depicted for example in FIG. 14. As discussed above, this latter shape may be any closed, two-dimensional shape, and it should be understood that the horizontal profile may vary as the hole is traversed along an axis passing through the hole from surface to surface of the guide. Thus for example, the hole may have an elliptical or elongated shape on the top surface to accommodate off-axis insertion of a drill, and may converge on a circular shape at a bottom surface of the guide (where the guide contacts a target surface) to accurately position a drill on the target surface.

In one aspect, the layer may have a thickness less than the diameter at the narrowest section. The layer may instead have a thickness greater than the diameter at the narrowest section. The layer may also or instead have a thickness greater or less than the diameter at the widest section. The diameter at the widest section may be at least ten percent greater than the diameter at the narrowest section, twenty five percent greater than the diameter at the narrowest section, fifty percent greater than the varying diameter at the narrowest section, or any other ratio suitable for use as generally described herein. The widest section may be on a top layer of the guide and the narrowest section may be on the bottom layer of the guide. Alternatively stated, the narrowest section may be at a surface of the guide proximal to a location where an axial trajectory meets a target surface of a surgical site. Or the narrowest section may be at a surface of the guide distal to the location where the axial trajectory meets the target surface of the surgical site. In other embodiments, the narrowest section may be between a top surface and a bottom surface of a layer of the guide, such as with the compound profiles discussed above.

The surgical guide 1300 may also include alignment marks (not shown), such as the alignment marks described below, to assist a user in aligning a tool to a desired trajectory.

Figure 14:
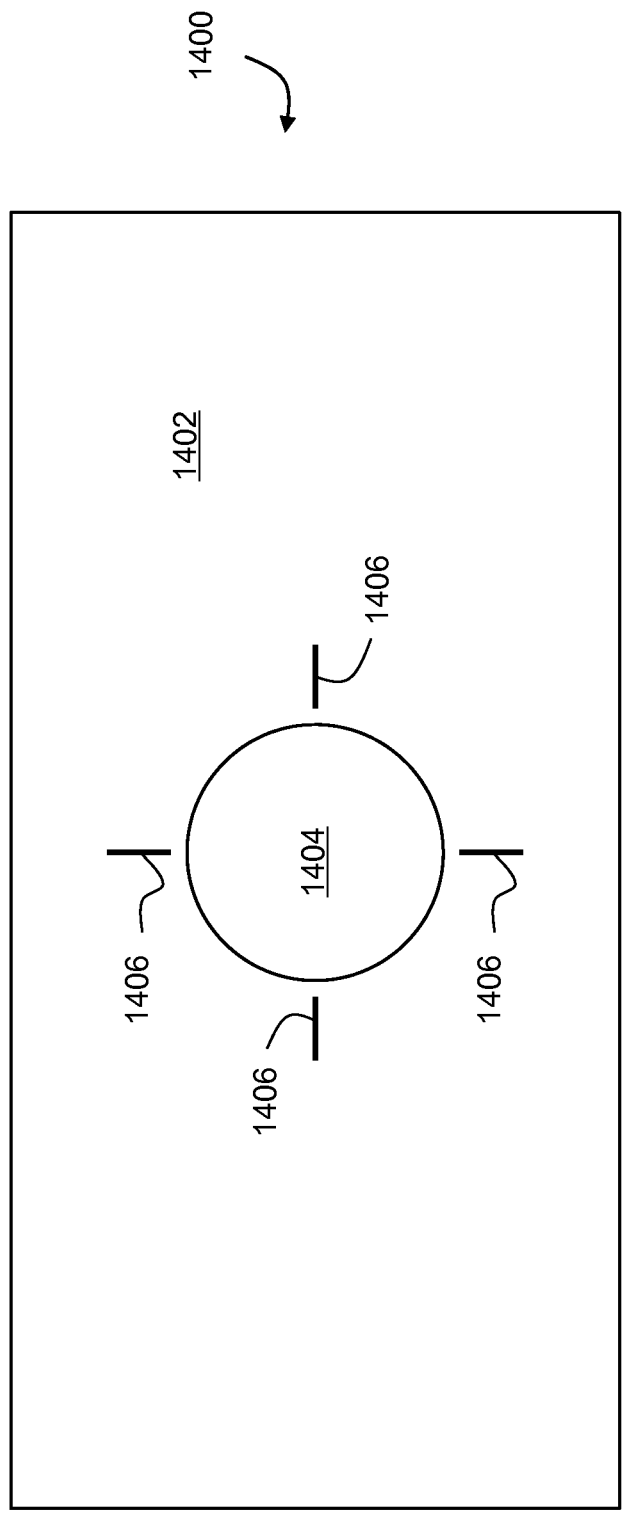
FIG. 14 shows alignment marks for a hole in a surgical guide.

FIG. 14 shows alignment marks for a hole in a surgical guide. A device 1400 may include a surface 1402, which may be a top or visible surface that can be viewed by a user of the surgical guide during use. The device 1400 may include a hole 1404 that serves as a surgical guide as generally described above. In addition, the device may include one or more visible alignment marks 1406 to assist a user in locating a center of the hole 1404 during use, or otherwise assist a user in centering a tool such as a cutting tool on the axial trajectory. While depicted in a crosshair pattern, it will be appreciated that more or fewer marks may be provided such as a grid or other regular pattern of lines or other shapes. The visible alignment marks 1406 may include raised or lowered (e.g., three-dimensional) surface features and/or colored or other visual markings rendered in ink, or any other suitable markings, surface treatment or the like that are visible to a user. While a single layer is depicted, it will be further understood that the visible alignment marks 1406 may be provided on one or more layers of a multi-layer surgical guide, or any of the other guide devices described herein.

Figure 15:
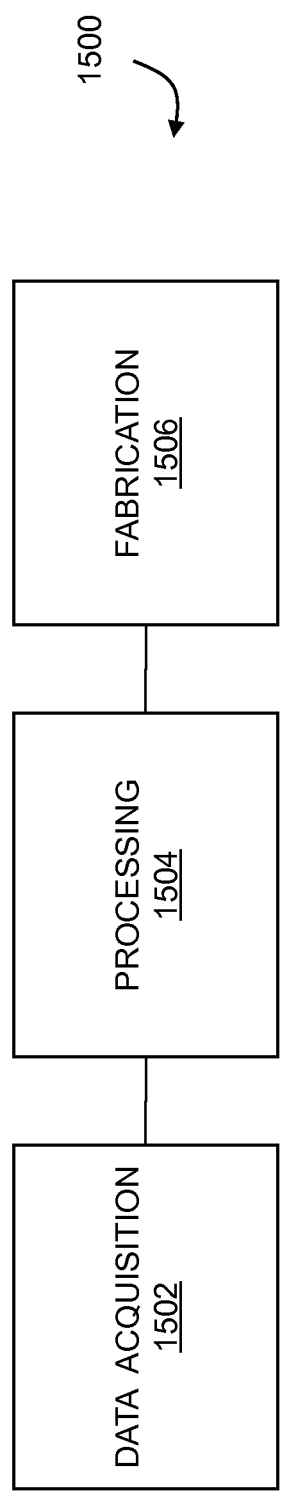
FIG. 15 shows a system for creating a surgical guide.

FIG. 15 shows a system for creating a surgical guide. The above methods for fabricating guides may in general be realized using a system 1500 with a variety of components. For example, the system 1500 may include a data acquisition system 1502, a processing system 1504, and a computerized fabrication system 1506.

The system 1500 may optionally include a data acquisition system 1502. The data acquisition system 1502 may, for example, include any of the data acquisition systems described above. This may include three-dimensional scanning systems for obtaining surface data from dentition and surrounding dental structures, or this may include computerized tomography systems for capturing volumetric data and/or subsurface structural data (e.g., from beneath the target surface of a surgical site) that may be usefully employed in the methods described herein. The data acquisition system 1502 may also or instead, include a physical interface such as a keyboard and mouse for manual entry of information concerning a patient, a guide, a surgical plan, and so forth.

The system 1500 may optionally include a processing system 1504 such as a computer or other suitable processor or processing circuitry for performing functions associated with the fabrication of a surgical guide. This may include, for example a computer executing case planning software or providing other tools to assist a clinician or lab technician in receiving data, planning a surgical procedure, and specifying a drill guide for the surgical procedure.

The system 1500 may optionally include a computerized fabrication system 1506. This may be any computer-controlled fabrication system including rapid prototyping systems using, e.g., stereo-lithography, three-dimensional printing, computerized milling, and so forth, or any other computer-controlled machine or combination of machines described herein. It will also be appreciated from the methods described above, that many steps in the methods described above may also, or instead, include manual procedures such as the creation of vacuum-formed molds from dental models and so forth.

It will be appreciated that many of the above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the various systems described above, or all of the functionality may be integrated into a dedicated, standalone device. All such permutations and combinations are intended to fall within the scope of the present disclosure.

In other embodiments, disclosed herein are computer program products comprising computer-executable code or computer-usable code that, when executing on one or more computing devices (such as the devices/systems described above), performs any and/or all of the steps described above. The code may be stored in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

It will be appreciated that the methods and systems described above are set forth by way of example and not of limitation. Numerous variations, additions, omissions, and other modifications will be apparent to one of ordinary skill in the art. Thus, for example, while dental implant procedures are clearly contemplated, this disclosure is not limited to oral surgery, but may facilitate any osteotomy, bone surgery, bone replacement, or other surgical procedure requiring drilling into bone or hard tissue, or more generally any procedure involving alignment of a tool to a desired trajectory. In addition, the order or presentation of method steps in the description and drawings above is not intended to require this order of performing the recited steps unless a particular order is expressly required or otherwise clear from the context.

While particular embodiments of the present invention have been shown and described, it will be apparent to those skilled in the art that various changes and modifications in form and details may be made therein without departing from the spirit and scope of the invention as defined by the following claims. The claims that follow are intended to include all such variations and modifications that might fall within their scope, and should be interpreted in the broadest sense allowable by law.

What is claimed is:

1. A method comprising:
   obtaining three-dimensional data from a surgical site;
   determining an axial trajectory for an implant to be placed in the surgical site based upon the three-dimensional data; and fabricating a device including a shell of single-piece construction formed to dentition around the surgical site, the shell including:

a surgical guide formed of a hole in a thin layer spaced apart from the target surface when placed for use at the surgical site, wherein the hole completely surrounds the axial trajectory and aligns a tool to the axial trajectory at a point along the axial trajectory while permitting movement of the tool away from the axial trajectory at one or more points along the axial trajectory away from the thin layer, wherein the thin layer has a thickness less than a radius of the hole;

an interior space along the axial trajectory formed between the thin layer and the target surface when the surgical guide is placed for use at the surgical site;

a second layer including a second hole, wherein the second layer is positioned between the thin layer and the target surface and the second hole is aligned to the axial trajectory when the surgical guide is placed for use at the surgical site;

a window in a side of the device for access to the interior space; and a support formed of at least one of the thin layer and the second layer and shaped according to the three-dimensional data to secure the surgical guide in relation to the surgical site.

2. The method of claim 1 wherein the three-dimensional data includes non-surface, interior data from within one or more dental structures.

3. The method of claim 1 wherein access to the interior space includes physical access.

4. The method of claim 1 wherein access to the interior space includes visual access.

5. The method of claim 1 wherein the window provides a view of the axial trajectory where the axial trajectory intersects the target surface when the device is placed for use at the surgical site.

6. The method of claim 1 wherein the window provides a view of the axial trajectory where the axial trajectory intersects the thin layer.

7. The method of claim 1 wherein the window includes a transparent surface of the device.

8. The method of claim 1 wherein the axial trajectory is a trajectory of a surgical drill into a dental implant site.

9. The method of claim 1 wherein the surgical site includes a dental implant site.

10. The method of claim 1 wherein the support is shaped and sized to provide bone support for the surgical guide.

11. The method of claim 1 wherein the support is shaped and sized to provide soft tissue support for the surgical guide.

12. The method of claim 1 wherein the window is positioned between the thin layer and the target surface.

13. The method of claim 1 wherein the window is positioned between the thin layer and the second layer, and wherein the second layer abuts the target surface.

14. The method of claim 1 wherein the interior space includes a volume between the thin layer and the target surface that permits an insertion of the tool off-axis from the axial trajectory.

15. The method of claim 1 wherein the surgical guide includes a plurality of holes in the thin layer for a plurality of axial trajectories at different locations in a dental arch.

16. The method of claim 1 further comprising fabricating a plurality of surgical guides, each including a progressively larger hole to align one of a number of progressively larger diameter drills to the axial trajectory.

17. The method of claim 1 wherein the support is shaped and sized to provide tooth support for the surgical guide.

* * * * *